United States Patent [19]
Fischer et al.

[11] Patent Number: 5,565,450
[45] Date of Patent: Oct. 15, 1996

[54] 5-ARYL-1,3-THIAZINE DERIVATIVES

[75] Inventors: Reiner Fischer, Monheim; Folker Lieb, Leverkusen; Michael Ruther, Monheim; Jörg Stetter, Wuppertal; Christoph Erdelen, Leichlingen; Ulrike Wachendorff-Neumann, Bonn; Markus Dollinger, Leverkusen; Klaus Lürssen, Bergisch Gladbach, all of Germany; Hans-Joachim Santel, West Haven, Conn.

[73] Assignee: Bayer Aktiengesellschaft, Leverkusen, Germany

[21] Appl. No.: 448,621

[22] PCT Filed: Dec. 10, 1993

[86] PCT No.: PCT/EP93/03483

§ 371 Date: Jun. 6, 1995

§ 102(e) Date: Jun. 6, 1995

[87] PCT Pub. No.: WO94/14785

PCT Pub. Date: Jul. 7, 1994

[30] Foreign Application Priority Data

Dec. 23, 1992 [DE] Germany ............... 42 43 818.7

[51] Int. Cl.$^6$ .............. A01N 43/86; C07D 279/06; C07D 417/12
[52] U.S. Cl. .............. 514/227.2; 544/54
[58] Field of Search ............... 544/54; 514/227.2

[56] References Cited

FOREIGN PATENT DOCUMENTS 0010420  4/1980  European Pat. Off. .
0245901  11/1987  European Pat. Off. .
0503958  9/1992  European Pat. Off. .

OTHER PUBLICATIONS

Ketcham et al, "Synthesis of Heterocycles. etc", J. Heterocy. Chem (1973), 10(2), 223–224.

Ziegler et al, "Synthesis of heterocycles. etc" CA60:15863d (1964).

E. Ziegler, et al., Monatshefte Für Chemie, vol. 95, No. 1, pp. 147–155, (1964).

*Primary Examiner*—Patricia L. Morris
*Attorney, Agent, or Firm*—Sprung Horn Kramer & Woods

[57] ABSTRACT

The present invention relates to the new substituted 5-aryl-1,3-thiazine derivatives of general formula (I)

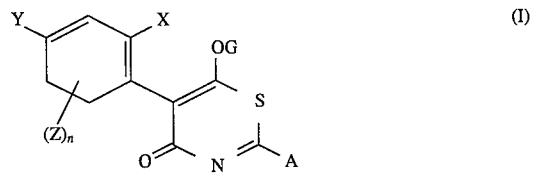

in which

A, G, X, Y and Z are defined in the specification and their use as pesticides, preferably as arthropodicides, nematicides and herbicides, as well as ecto- and endoparasiticides.

18 Claims, No Drawings

5-ARYL-1,3-THIAZINE DERIVATIVES

The invention relates to new 5-aryl-1,3-thiazine derivatives, to processes for their preparation and to their use as pesticides.

Certain 5-phenyl-1,3-thiazine derivatives which are unsubstituted in the phenyl ring have already been disclosed (cf. E. Ziegler and E. Steiner, Monatsh. 95, 147 (1964), R. Ketcham, T. Kappe and E. Ziegler, J. Heterocycl. Chem. 10, 223 (1973)), but a possible use as pesticides is not mentioned for these, compounds.

There have now been found the new substituted 5-aryl-1,3-thiazine derivatives of the general formula (I)

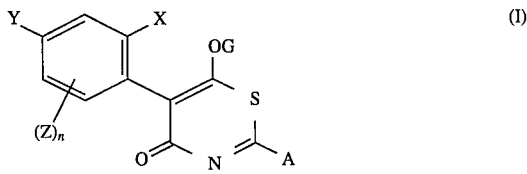

in which
A represents an optionally substituted radical from the series consisting of alkyl, cycloalkyl, alkenyl, alkinyl, arylalkyl, aryl, hetarylalkyl and hetaryl, or represents an optionally substituted radical from the series consisting of alkoxy, cycloalkoxy, alkenyloxy, alkinyloxy, arylalkenloxy, aryloxy, hetarylalkyloxy and hetaryloxy or represents an optionally substituted radical from the series consisting of alkylthio, cycloalkylthio, alkenylthio, alkinylthio, arylalkylthio, arylthio, hetarylalkylthio and hetarylthio, or represents the groups

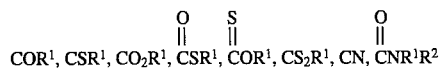

and $CSNR^1R^2$ in which
$R^1$ and $R^2$ independently of one another represent optionally substituted radicals from the series consisting of alkyl, alkenyl, arylalkyl, aryl, hetarylalkyl and hetaryl or
$R^1$ and $R^2$ together represent an optionally substituted alkylene group which can be interrupted by one or more hetero atoms;
X represents halogen, alkyl or alkoxy;
Y represents hydrogen, halogen, alkyl, halogenoalkyl or alkoxy;
Z represents hydrogen, halogen, alkyl or alkoxy;
n represents an integer 1, 2 or 3; and
G represents hydrogen, a metal ion equivalent, an ammonium ion or a group —$COR^3$,

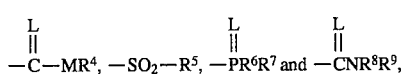

in which
represents optionally substituted radicals from the series consisting of alkyl, alkenyl, alkoxyalkyl, polyalkoxyalkyl, alkylthioalkyl, cycloalkyl which is optionally interrupted by one or more hetero atoms and optionally substituted, arylalkyl, aryl, hetarylalkyl, hetaryl, aryloxyalkyl and hetaryloxyalkyl;
$R^4$ represent optionally substituted radicals from the series consisting of alkyl, alkenyl, alkoxyalkyl, polyalkoxyalkyl, aryl and arylalkyl;
$R^5$, $R^6$ and $R^7$ independently of one another represent optionally substituted radicals from the series consisting of alkyl, alkoxy, alkenoxy, alkylthio, alkylamino, dialkylamino, alkenylthio, alkinylthio, cycloalkylthio, aryl, aryloxy and arylthio;
$R^8$ and $R^8$ independently of one another represent hydrogen or optionally substituted radicals from the series consisting of alkyl, alkenyl, cycloalkyl, alkoxyalkyl, aryl or arylalkyl, or together form an optionally substituted alkylene group which can be interrupted by one or more hetero atoms or hetero groups;
L represents oxygen or sulphur; and
M represents oxygen or sulphur.

Depending on the substituents, the compounds of the general formula (I) can exist as geometric and/or optical isomers or variously composed mixtures of isomers. The invention claimed extends to the pure isomers as well as the isomer mixtures, their preparation, their use, and compositions containing them. For the sake of simplicity, however, the following text will always mention compounds of the formula (I), even though this is to be understood as meaning the pure compounds and, if appropriate, also mixtures containing various proportions of isomeric compounds.

Furthermore, it has been found that the new compounds of the general formula (I) display a very potent activity as pesticides, preferably as insecticides, acaricides, nematicides and herbicides, as well as ecto- and endoparasiticides.

Furthermore, it has been found that the new 5-aryl-1,3-thiazine derivatives of the general formula (I) are obtained when, a) to prepare the compounds in which G represents hydrogen, thioamides of the general formula (II)

in which
A has the abovementioned meaning
are reacted with ketenic acid halides of the general formula (III)

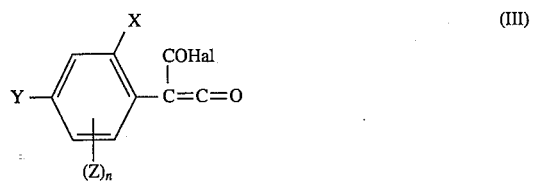

in which
X, Y, Z and n have the abovementioned meanings and
Hal represents halogen (preferably chlorine or bromine)
in the presence of a diluent and if appropriate in the presence of an acid acceptor; and b) to prepare the compounds of the general formula (I) in which G represents —$COR^3$,
compounds of the general formula (I) in which G represents hydrogen (which can be obtained by variant a)) are reacted
α) with acid halides of the general formula (IV)

in which
$R^3$ has the abovementioned meaning and
Hal represents halogen (preferably chlorine or bromine), or β) with carboxylic anhydrides of the general formula (V)

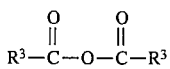  (V)

in which
R³ has the abovementioned meaning,
if appropriate in the presence of a diluent and if appropriate in the presence of an acid-binding agent; and c) to prepare the compounds of the general formula (I) in which G represents —C(L)—MR⁴ where L denotes oxygen and M and R⁴ have the abovementioned meaning,
compounds of the general formula (I) in which G represents hydrogen (which can be obtained by variant a))
are reacted with compounds of the general formula (VI)

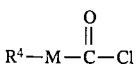  (VI)

in which
R⁴ and M have the abovementioned meanings,
if appropriate in the presence of a diluent and if appropriate in the presence of an acid-binding agent; and (d) to prepare the compounds of the general formula (I) in which G represents —C(L)—MR⁴ where L denotes sulphur and M and R⁴ have the abovementioned meaning,
compounds of the general formula (I) in which G represents hydrogen (which can be obtained by variant a)), are reacted
α) with compounds of the general formula (VII)

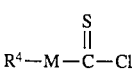  (VII)

in which
R⁴ and M have the abovementioned meanings,
if appropriate in the presence of a diluent and if appropriate in the presence of an acid-binding agent, or
β) with carbon disulphide (CS₂) and subsequently with alkyl halides of the general formula (VIII)

  (VIII)

in which
R⁴ has the abovementioned meaning and
Hal¹ represents halogen (preferably chlorine, bromine and iodine),
if appropriate in the presence of a diluent and if appropriate in the presence of an acid-binding agent;

e) to prepare compounds of the general formula (I) in which G represents —SO₂R⁵,
compounds of the general formula (I) in which G represents hydrogen (which can be obtained by variant a)), are reacted
with sulphonyl chlorides of the general formula (IX) in which

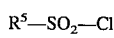  (IX)

in which
R⁵ has the abovementioned meaning,
if appropriate in the presence of a diluent and if appropriate in the presence of an acid-binding agent; and f) to prepare compounds of the general formula (I) in which G represents —P(L)—R⁶R⁷,
compounds of the general formula (I) in which G represents hydrogen (which can be obtained by variant a))
are reacted with compounds of the general formula (X)

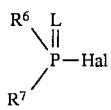  (X)

in which
R⁶, R⁷ and L have the abovementioned meanings and
Hal represents halogen (preferably chlorine or bromine),
if appropriate in the presence of a diluent and if appropriate in the presence of an acid-binding agent; and g) to prepare compounds of the general formula (I) in which G represents a metal ion equivalent or an ammonium ion,
compounds of the general formula (I) in which G represents hydrogen (which can be obtained by variant a)) are reacted with metal hydroxides or amines (preferably mono-, di- or trialkylamines); and h) to prepare compounds of the general formula (I) in which G represents —C(L)NR⁸R⁹,
compounds of the general formula (I) in which G represents hydrogen (which can be obtained by variant a)) are reacted
α) with compounds of the general formula (XI)

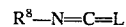  (XI)

in which
R⁸ and L have the abovementioned meanings,
if appropriate in the presence of a diluent and if appropriate in the presence of a catalyst; or
α) with compounds of the general formula (XII)

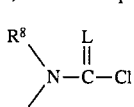  (XII)

in which
R⁸, R⁹ and L have the abovementioned meanings,
if appropriate in the presence of a diluent and if appropriate in the presence of an acid-binding agent.

Alkyl as such or as moiety of another group (for example alkoxy, alkylthio and halogenoalkyl) denotes, in the general formulae, straight-chain or branched alkyl having advantageously 1 to 20, particularly advantageously 1 to 18 and very particularly advantageously 1 to 16 carbon atoms. Alkyl preferably contains 1 to 8, particularly preferably 1 to 6 and very particularly preferably 1 to 4 carbon atoms, specific mentioned being made of methyl, ethyl, n- and i-propyl and n-, i-, s- and t-butyl.

Cycloalkyl as such or as moiety of another group (for example cycloalkylthio) contains, in the general formulae, preferably 3 to 10, particularly preferably 3 to 7 and very particularly preferably 3 to 6 carbon atoms, specific mention being made of cyclopropyl, cyclobutyl, cyclopentyl and cyclohexyl. In the event that cycloalkyl is interrupted by one or more hetero atoms or hetero groups, these are identical or different, preferably 1 or 2, hetero atoms or hetero groups. Hetero atoms are preferably oxygen or sulphur, and hetero groups preferably NH or $NC_1$–$C_4$-alkyl.

Alkenyl and alkinyl are such or as moiety of another group (such as alkenylthio and alkinylthio) denote, in the general formulae, straight-chain or branched alkenyl and alkinyl having preferably 1 double or triple bond, respectively, and preferably 2 to 8, in particular 3 to 6 and very particularly preferably 3 or 4 carbon atoms, specific mentioned being made of the allyl and propargyl groups.

Aryl as such or as moiety of another group (such as aryloxy or arylthio) denotes, in the general formulae, preferably naphthyl and phenyl, particularly preferably phenyl.

Aralkyl denotes, in the general formulae, preferably naphthylalkyl or phenylalkyl, particularly preferably phenylalkyl. The alkyl moiety is straight-chain or branched and contains preferably 1 to 6, particularly preferably 1 to 4 and very particularly preferably 1 or 2 carbon atoms. Specific mention may be made of benzyl and phenylethyl.

Hetaryl as such or as moiety of another group (such as hetarylalkyl or hetaryloxyalkyl) denotes, in the general formulae, heteromatic 5- to 7-membered rings having preferably 1 to 3, in particular 1 or 2, identical or different hetero atoms. Hetero atoms are preferably oxygen, sulphur or nitrogen. Pyrryl, furyl, thienyl, thiazolyl, pyridyl, pyrazolyl and pyrimidinyl may be mentioned by way of example and as being preferred.

Hetaryl in hetarylalkyl and hetaryloxyalkyl of the general formulae has the abovementioned meaning. The alkyl moieties are straight-chain or branched and contain preferably 1 to 6, particularly preferably 1 to 4 and very particularly preferably 1 or 2, carbon atoms, specific mentioned being made of hetarylmethyl and hetaryloxymethyl.

The aryl moieties in alkylthio, alkoxy, halogenoalkyl, halogenoalkyl, alkoxyalkyl, alkylthioalkyl, polyalkoxyalkyl, aryloxyalkyl, hetaryloxyalkyl, alkylamino and dialkylamino have the meanings mentioned above in the case of alkyl.

Halogenoalkyl and halogenoalkyl contain preferably 1 to 8, in particular 1 to 5 and very particularly preferably 1 to 5, identical or different halogen atoms. Halogen atoms are preferably fluorine, chlorine, bromine and/or iodine, in particular fluorine, chlorine and/or bromine and very particularly preferably fluorine and/or chlorine. Examples which may be mentioned are trifluoromethyl, chloro-difluoromethyl, bromomethyl, 2,2,2-trifluoroethyl and pentafluoroethyl.

The aryl or hetaryl moieties in aryloxyalkyl and hetaryloxyalkyl, respectively, of the general formulae have the meanings given above for these radicals.

Alkenyl, alkinyl and cycloalkyl in alkenylthio, alkinylthio and cycloalkylthio of the general formulae have the meanings given above in the case of the radicals in question.

The aryl moieties in aryloxy and arylthio of the general formulae have the meanings given above for aryl.

The polyalkoxy radicals of the general formulae contain preferably 2 to 4, in particular 2 to 3 and very particularly preferably 2 alkoxy radicals, the alkyl radicals having the abovementioned meaning.

If two substituents of the general formulae (for example A and B, $R^1$ and $R^2$ and $R^8$ and $R^9$) together form an alkylene or alkenylene group, this group is straight-chain or branched and contains preferably 2 to 7, in particular 2 to 6 and very particularly preferably 2 to 5, carbon atoms. The alkenylene groups contain one or more, preferably 1 or 2, in particular 1 double bond. The alkylene or alkenylene groups can be interrupted by one or more identical or different hetero atoms or hetero groups, such as oxygen, sulphur or nitrogen and —OCO—, or can contain such groups. Examples which may be mentioned are —$(CH_2)_4$—, —$(CH_2)_5$—, —$(CH_2)_2$—O—$(CH_2)_2$— and —$(CH_2)_2$—S—$(CH_2)_2$— or —O—CO—$CH_2$—.

Unless otherwise defined, halogen denotes, in the general formulae, fluorine, chlorine, bromine and/or iodine, preferably fluorine, chlorine and/or bromine, very particularly preferably fluorine and/or chlorine.

A metal ion equivalent denotes, in the general formulae, an equivalent of a metal cation, preferably the cation of an alkaline earth metal or alkali metal, in particular of a calcium, magnesium, sodium or potassium cation, very particularly preferably a calcium, sodium or potassium cation.

An ammonium ion preferably denotes, in the general formulae, a monoalkyl-, dialkyl- or trialkylammonium ion, the alkyl radicals containing preferably 1 to 6, in particular 1 to 4 and very particularly preferably 1 or 2, carbon atoms. The alkyl radicals can be mono- or polysubstituted, preferably monosubstituted, substituents which may be mentioned preferably being hydroxyl or halogen.

n in the general formulae preferably represents 1 or 2, particularly preferably 1, the substituent Z preferably being in the 6-position of the phenyl ring.

The optionally substituted radicals mentioned in the general formulae can have one or more, preferably 1 to 3, in particular 1 or 2, identical or different substituents. The following substituents may be mentioned by way of example and as being preferred:

alkyl having preferably 1 to 8, in particular 1 to 6 and very particularly preferably 1 to 4, carbon atoms, such as methyl, ethyl, n- and i-propyl, and n-, i- and t-butyl; alkoxy having preferably 1 to 8, in particular 1 to 6 and very particularly preferably 1 to 4, carbon atoms, such as methoxy, ethoxy, n- and i-propyloxy, and n-, i- and t-butyloxy; alkylthio having preferably 1 to 8, in particular 1 to 6 and very particularly preferably 1 to 4, carbon atoms, such as methylthio, ethylthio, n- and i-propylthio, and n-, i- and t-butylthio; halogenoalkyl and halogenoalkoxy having preferably 1 to 8, in particular 1 to 6 and very particularly preferably 1 to 4, carbon atoms and preferably 1 to 7, in particular 1 to 5 and very particularly preferably 1 to 3, carbon atoms, the halogen atoms being identical or different and preferably representing fluorine, chlorine or bromine, in particular fluorine, such as trifluoromethyl or trifluoromethoxy; hydroxyl; amino; halogen, preferably fluorine, chlorine, bromine and iodine, in particular fluorine, chlorine and bromine; cyano, nitro, phenyl which is optionally substituted by the abovementioned radicals; alkylcarbonyloxy having preferably 1 to 6, in particular 1 to 4 and very particularly preferably 1 or 2, carbon atoms in the alkyl group, or a heteroaliphatic or heteroaromatic radical, such as pyridyl, furyl or tetrahydrofuryl.

A in the general formulae preferably represents radicals from the series consisting of $C_1$–$C_{10}$-alkyl, $C_3$–$C_{10}$-alkenyl, $C_3$–$C_{10}$-alkinyl, and $C_3$–$C_{10}$-cycloalkyl which are optionally substituted by halogen; or represents radicals from the series consisting of phenyl, naphthyl, hetaryl, phenyl-$C_1$–$C_6$-alkyl and hetaryl-$C_1$–$C_6$-alkyl which are optionally substituted by halogen, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy and/or CN, or represents radicals from the series consisting of $C_1$–$C_{10}$-alkoxy, $C_3$–$C_{10}$-alkenyloxy, $C_3$–$C_{10}$- alkinyl-oxy, and $C_3$-$C_{10}$-cycloalkoxy which are optionally substituted by halogen; or represents radicals from the series consisting of phenyloxy, naphthyloxy, heteryloxy, phenyl-$C_1$-$C_6$-alkoxy and hetaryl-$C_1$-$C_6$-alkoxy which are optionally substituted by halogen, nitro, $C_1$-$C_8$-alkyl, $C_1$-$C_8$-alkoxy, $C_1$-$C_8$-alkylthio, $C_1$-$C_8$-halogenoalkyl, $C_1$-$C_8$-halogenoalkoxy and/or CN, or represents radicals from the series consisting of $C_1$-$C_{10}$-alkylthio, $C_3$-$C_{10}$-alkenylthio, $C_3$-$C_{10}$-alkinylthio and $C_3$-$C_{10}$-cycloalkylthio which are optionally substituted by halogen, or represents radicals from the series consisting of phenylthio, naphthylthio, hetarylthio, phenyl-$C_1$-$C_6$-alkylthio and hetaryl-$C_1$-$C_6$-alkylthio which are optionally substituted by halogen, nitro, $C_1$-$C_8$-alkyl, $C_1$-$C_8$-alkoxy, $C_1$-$C_8$-alkylthio, $C_1$-$C_8$-halogenoalkyl, $C_1$-$C_8$-halogenoalkoxy and/or CN, or represents the groups $COR^1$, $CSR^1$, $CO_2R^1$,

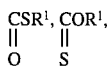

$CS_2R^1$, CN, $CONR^1R^2$ and $CSNR^1R^2$, where $R^1$ and $R^2$ independently of one another represent radicals from the series consisting of $C_1$-$C_{10}$-alkyl and $C_3$-$C_{10}$-alkenyl which are optionally substituted by halogen; or represent radicals from the series consisting of phenyl, naphthyl, hetaryl, phenyl-$C_1$-$C_6$-alkyl and hetaryl-$C_1$-$C_6$-alkyl which are optionally substituted by halogen, nitro, $C_1$-$C_8$-alkyl, $C_1$-$C_8$-alkoxy, $C_1$-$C_8$-alkylthio, $C_1$-$C_8$-halogenoalkyl, $C_1$-$C_8$-halogenoalkoxy and/or CN; or $R^1$ and $R^2$ together represent a $C_2$-$C_7$-alkylene group which is optionally interrupted by nitrogen, oxygen or sulphur.

A in the general formulae very particularly preferably represents radicals from the series consisting of $C_3$-$C_8$-alkyl, $C_3$-$C_8$-alkenyl, $C_3$-$C_8$-alkinyl, and $C_3$-$C_8$-cycloalkyl which are optionally substituted by halogen; or represents radicals from the series consisting of phenyl, naphthyl, hetaryl, phenyl-$C_1$-$C_4$-alkyl and hetaryl-$C_1$-$C_4$-alkyl which are optionally substituted by halogen, nitro, $C_1$-$C_4$-alkyl, $C_1$-$C_4$-alkoxy, $C_1$-$C_4$-alkylthio, $C_1$-$C_4$-halogenoalkyl, $C_1$-$C_4$-halogenoalkoxy and/or CN, or represents radicals from the series consisting of $C_1$-$C_6$-alkoxy, $C_3$-$C_6$-alkenyloxy, $C_3$-$C_6$-alkinyloxy, and $C_3$-$C_6$-cycloalkoxy which are optionally substituted by halogen; or represents radicals from the series consisting of phenyloxy, naphthyloxy, phenyl-$C_1$-$C_2$-alkoxy and thienyloxy, furyloxy, thiazolyloxy, pyridyloxy and pyrazolyloxy which are optionally substituted by halogen, nitro, $C_1$-$C_4$-alkyl, $C_1$-$C_4$-alkoxy, $C_1$-$C_4$-alkylthio, $C_1$-$C_4$-halogenoalkyl, $C_1$-$C_4$-halogenoalkoxy and/or CN; or represents radicals from the series consisting of $C_1$-$C_6$-alkylthio, $C_3$-$C_6$-alkenylthio, $C_3$-$C_6$-alkinylthio and $C_3$-$C_6$-cycloalkylthio which are optionally substituted by halogen, or represents radicals from the series consisting of phenylthio, naphthylthio, phenyl-$C_1$-$C_2$-alkylthio, thienylthio, thienyl-$C_1$-$C_2$-alkylthio, furylthio, thiazolylthio, pyridylthio and pyrazolylthio which are optionally substituted by halogen, nitro, $C_1$-$C_4$-alkyl, $C_1$-$C_4$-alkoxy, $C_1$-$C_4$-alkylthio, $C_1$-$C_4$-halogenoalkyl, $C_1$-$C_4$-halogenoalkoxy and/or CN, or represents the groups $COR^1$, $CSR^1$, $CO_2R^1$

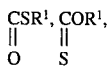

$CS_2R^1$, CN, $CONR^1R^2$ and $CSNR^1R^2$, where $R^1$ and $R^2$ independently of one another represent radicals from the series consisting of $C_1$-$C_6$-alkyl and $C_3$-$C_6$-alkenyl which are optionally substituted by halogen; or represent phenyl which is optionally substituted by halogen, nitro, $C_1$-$C_4$-alkyl $C_1$-$C_4$-alkoxy, $C_1$-$C_4$-alkylthio $C_1$-$C_4$-halogenoalkyl, $C_1$-$C_4$-halogenoalkoxy and/or CN.

In a particularly emphasized embodiment of the present invention, A represents radicals from the series consisting of phenyl, phenoxy and phenylthio which are optionally substituted by halogen In the general formulae, X preferably represents halogen, $C_1$-$C_6$-alkyl or $C_1$-$C_6$-alkoxy, particularly preferably halogen, $C_1$-$C_4$-alkyl or $C_1$-$C_4$-alkoxy, and very particularly preferably fluorine, chlorine, bromine, methyl, ethyl, n- and i-propyl, methoxy or ethoxy, and, in a particularly emphasized embodiment of the invention, methyl.

In the general formulae, Y preferably represents hydrogen, halogen, $C_1$-$C_6$-alkyl, $C_1$-$C_6$-alkoxy or $C_1$-$C_6$-halogenoalkyl, particularly preferably hydrogen, halogen, $C_1$-$C_4$-alkyl, $C_1$-$C_4$-halogenoalkyl or $C_1$-$C_4$-alkoxy, and very particularly preferably hydrogen, fluorine, chlorine, bromine, $C_1$-$C_4$-alkyl or trifluoromethyl, and, in a particularly emphasized embodiment of the invention, methyl.

In the general formulae, Z preferably represents hydrogen, halogen, $C_1$-$C_6$-alkyl or $C_1$-$C_6$-alkoxy, particularly preferably hydrogen, halogen, $C_1$-$C_4$-alkyl or $C_1$-$C_4$-alkoxy, and, very particularly preferably hydrogen, fluorine, chlorine, bromine, $C_1$-$C_4$-alkyl, methoxy or ethoxy, and, in a particular embodiment of the invention, methyl (preferably in the (6-position of the phenyl ring).

In the general formulae, n represents 1, 2 or 3, preferably 1 or 2, and very particularly preferably 1 (Z preferably being in the 6-position of the phenyl ring).

G in the general formulae preferably represents hydrogen or one of the groups —$COR^3$,

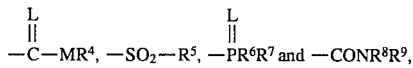

particularly preferably hydrogen, —$COR^3$,

or $CONR^8R^9$ and very particularly hydrogen,—$COR^3$

and, in a particularly emphasized embodiment of the invention, hydrogen.

$R^3$ in the general formulae preferably represents optionally halogen-substituted radicals from the series consisting of $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, $C_1$-$C_8$-polyalkoxy-$C_1$-$C_8$-alkyl and $C_3$-$C_8$-cycloalkyl which is optionally interrupted by oxygen and/or sulphur; or represents phenyl which is optionally substituted by halogen, nitro, $C_1$-$C_6$-alkyl, $C_1$-$C_6$-alkoxy, $C_1$-$C_6$-halogenoalkyl and/or $C_1$-$C_6$-halogenoalkoxy; or represents phenyl-$C_1$-$C_6$-alkyl which is optionally substituted by halogen, $C_1$-$C_6$-alkyl, $C_1$-$C_6$-alkoxy, $C_1$-$C_6$-halogenoalkyl and/or $C_1$-$C_6$-halogenoalkoxy; or represents hetaryl which is optionally substituted by halogen and/or $C_1$-$C_6$-alkyl; or represents phenoxy-$C_1$-$C_6$-alkyl which is optionally substituted by halogen and/or $C_1$-$C_6$-alkyl, or represents hetaryloxy-$C_1$-$C_6$-alkyl which is optionally substituted by halogen amino and/or $C_1$-$C_6$-alkyl.

$R^3$ in the general formulae particularly preferably represents optionally halogen-substituted radicals from the series consisting of $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl, $C_1$–$C_6$-polyalkoxy-$C_1$–$C_6$-alkyl and $C_3$-Cycloalkyl which is optionally interrupted by oxygen and/or sulphur; or represents phenyl which is optionally substituted by halogen, nitro, $C_1$–$C_4$-alkyl, $C_1$–$C_4$-alkoxy, $C_1$–$C_3$-halogenoalkyl and/or $C_1$–$C_3$-halogenoalkoxy; or represents phenyl-$C_1$–$C_4$-alkyl which is optionally substituted by halogen, $C_1$–$C_4$alkyl, $C_1$–$C_4$-alkoxy, $C_1$–$C_3$-halogenoalkyl and/or $C_1$–$C_3$-halogenoalkoxy; or represents hetaryl which is optionally substituted by halogen and/or $C_1$–$C_6$-alkyl; or represents phenoxy-$C_1$–$C_5$-alkyl which is optionally substituted by halogen and/or $C_1$–$C_4$-alkyl, or represents hetaryloxy-$C_1$–$C_5$-alkyl which is optionally substituted by halogen, amino and/or $C_1$–$C_4$-alkyl.

$R^3$ in the general formulae very particularly preferably represents optionally fluorine- and/or chlorine-substituted radicals from the series consisting of $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, $C_1$–$C_4$-polyalkoxy-$C_1$–$C_6$-alkyl and $C_3$–$C_6$-cycloalkyl, optionally interrupted by 1 or 2 oxygen and/or sulphur atoms; or represents phenyl which is optionally substituted by fluorine, chlorine, bromine, nitro, $C_1$–$C_3$-alkyl, methoxy, ethoxy, trifluoromethyl and/or trifluoromethoxy; or represents phenyl-$C_1$–$C_3$-alkyl which is optionally substituted by fluorine, chlorine, bromine, $C_1$–$C_3$-alkyl, methoxy, ethoxy, trifluoromethyl and/or trifluoromethoxy; or represents radicals from the series consisting of pyridyl, pyrimidyl, thiazolyl and pyrazolyl which are optionally substituted by fluorine, chlorine, bromine, methyl and/or ethyl; or represents phenoxy-$C_1$–$C_4$-alkyl which is optionally substituted by fluorine, chlorine, methyl and/or ethyl, or represents radicals from the series consisting of pyridyloxy-$C_1$–$C_4$-alkyl, pyrimidyloxy-$C_1$–$C_4$-alkyl and thiazolyloxy-$C_1$–$C_4$-alkyl which are optionally substituted by fluorine, chlorine, amino, methyl and/or ethyl.

In a particularly emphasized embodiment of the present invention $R^3$ represents $C_1$–$C_6$-alkyl which can be substituted by halogen.

$R^4$ in the general formulae preferably represents radicals from the series consisting of $C_1$–$C_{20}$-alkyl, $C_2$–$C_{20}$-alkenyl, $C_1$–$C_8$-alkoxy-$C_1$–$C_8$-alkyl and $C_1$–$C_8$-polyalkoxy-$C_1$–$C_8$-alkyl which are optionally substituted by halogen, or represents radicals from the series consisting of phenyl and benzyl which are optionally substituted by halogen, nitro, $C_1$–$C_6$-alkyl, $C_1$–$C_6$-alkoxy and/or $C_1$–$C_6$-halogenoalkyl.

$R^4$ in the general formulae particularly preferably represents radicals from the series consisting of $C_1$–$C_{16}$-alkyl, $C_2$–$C_{16}$-alkenyl, $C_1$–$C_6$-alkoxy-$C_1$–$C_6$-alkyl and $C_1$–$C_6$-polyalkoxy-$C_1$–$C_6$-alkyl which are optionally substituted by halogen, or represents radicals from the series consisting of phenyl and benzyl which are optionally substituted by halogen, nitro, $C_1$–$C_4$-alkyl, $C_1$–$C_3$-alkoxy and/or $C_1$–$C_3$-halogenoalkyl.

$R^4$ in the general formulae very particularly preferably represents radicals from the series consisting of $C_1$–$C_{14}$-alkyl, $C_2$–$C_{14}$-alkenyl, $C_1$–$C_4$-alkoxy-$C_1$–$C_6$-alkyl and $C_1$–$C_4$-polyalkoxy-$C_1$–$C_6$-alkyl which are optionally substituted by fluorine and/or chlorine, or represents radicals from the series consisting of phenyl and benzyl which are optionally substituted by fluorine, chlorine, nitro, $C_1$–$C_3$-alkyl, methoxy, ethoxy and/or trifluoromethyl.

In a particularly emphasized embodiment of the invention, $R^4$ represents $C_1$–$C_6$-alkyl which can be substituted by halogen.

$R^5$, $R^6$ and $R^7$ in the general formulae independently of one another preferably represent radicals from the series consisting of $C_1$–$C_8$-alkyl, $C_1$–$C_8$-alkoxy, $C_1$–$C_8$-alkylthio, $C_1$–$C_8$-alkylamino, di-($C_1$–$C_8$)-alkylamino, $C_2$–$C_5$-alkenylthio, $C_2$–$C_5$-alkinylthio and $C_3$–$C_7$-cycloalkylthio which are optionally substituted by halogen, or represent radicals from the series consisting of phenyl, phenyloxy and phenylthio which are optionally substituted by halogen, nitro, cyano, $C_1$–$C_4$-alkoxy, $C_1$–$C_4$-alkylthio, $C_1$–$C_4$-halogenoalkoxy, $C_1$–$C_4$-halogenoalkylthio, $C_1$–$C_4$-alkyl and/or $C_1$–$C_4$-halogenoalkyl.

$R^5$, $R^6$ and $R^7$ in the general formulae independently of one another particularly preferably represent radicals from the series consisting of $C_1$–$C_6$-alkyl, $C_1$–$C_6$-alkoxy, $C_1$–$C_6$-alkylthio, $C_1$–$C_6$-alkylamino, di-($C_1$–$C_6$)-alkylamino, $C_2$–$C_6$-alkenylthio, $C_2$–$C_4$-alkinylthio and $C_3$–$C_6$-cycloalkylthio which are optionally substituted by halogen, or represent radicals from the series consisting of phenyl, phenyloxy and phenylthio which are optionally substituted by halogen, nitro, cyano, $C_1$–$C_3$-alkoxy, $C_1$–$C_3$-alkylthio, $C_1$–$C_3$-halogenoalkoxy, $C_1$–$C_3$-halogenoalkylthio, $C_1$–$C_3$-alkyl and/or $C_1$–$C_3$-halogenoalkyl.

$R^5$, $R^6$ and $R^7$ in the general formulae independently of one another very particularly preferably represent radicals from the series consisting of $C_1$–$C_4$-alkyl, $C_1$–$C_4$-alkoxy, $C_1$–$C_4$-alkylthio, $C_1$–$C_4$-alkylamino or di-($C_1$–$C_4$)-alkylamino which are optionally substituted by fluorine and/or chlorine, or represent radicals from the series consisting of phenyl, phenyloxy and phenylthio which are optionally substituted by halogen, nitro, cyano, $C_1$–$C_2$-alkoxy, $C_1$–$C_2$-alkylthio, $C_1$–$C_2$-fluoroalkoxy, $C_1$–$C_2$-chloroalkoxy, $C_1$–$C_2$-fluoroalkylthio, $C_1$–$C_2$-chloroalkylthio and/or $C_1$–$C_3$-alkyl.

In a particularly emphasized embodiment of the invention, $R^5$, $R^6$ and $R^7$ independently of one another represent $C_1$–$C_6$-alkyl which is optionally substituted by halogen.

$R^8$ and $R^9$ in the general formulae independently of one another preferably represent hydrogen, or represent radicals from the series consisting of $C_1$–$C_{20}$-alkyl, $C_1$–$C_{20}$-alkoxy, $C_3$–$C_{10}$-cycloalkyl, $C_2$–$C_8$-alkenyl and $C_1$–$C_8$-alkoxy-$C_1$–$C_8$-alkyl which are optionally substituted by halogen, or represent radicals from the series consisting of phenyl and benzyl which are optionally substituted by halogen, $C_1$–$C_{20}$-alkyl, $C_1$–$C_{20}$-halogenoalkyl and/or $C_1$–$C_{20}$-alkoxy, or $R^8$ and $R^9$ together form a $C_2$–$C_6$-alkylene group which can be interrupted by oxygen and/or sulphur.

$R^8$ and $R^9$ in the general formulae independently of one another particularly preferably represent hydrogen, or represent radicals from the series consisting of $C_1$–$C_{16}$-alkyl, $C_1$–$C_{16}$-alkoxy, $C_3$–$C_{16}$-cycloalkyl, $C_2$–$C_6$-alkenyl or $C_1$–$C_6$-alkoxy-$C_1$–$C_6$-alkyl which are optionally substituted by halogen, or represent radicals from the series consisting of phenyl and benzyl which are optionally substituted by halogen, $C_1$–$C_6$-alkyl, $C_1$–$C_6$-halogenoalkyl and/or $C_1$–$C_6$-alkoxy, or $R^8$ and $R^9$ together form a $C_2$–$C_6$-alkylene group which can be interrupted by oxygen and/or sulphur.

$R^8$ and $R^9$ in the general formulae independently of one another very particularly preferably represent hydrogen, or represent radicals from the series consisting of $C_1$–$C_{10}$-alkyl, $C_1$–$C_{10}$-alkoxy and $C_1$–$C_4$-alkoxy-$C_1$–$C_4$-alkyl which are optionally substituted by halogen, or represent radicals from the series consisting of phenyl and benzyl which are optionally substituted by halogen, $C_1$–$C_4$-alkyl, $C_1$–$C_4$-halogenoalkyl and/or $C_1$–$C_4$-alkoxy, or $R^8$ and $R^9$ together form a $C_2$–$C_4$-alkylene group which can be interrupted by oxygen and/or sulphur.

In a particularly emphasized embodiment of the invention, $R^8$ and $R^9$ independently of one another represent hydrogen or $C_1$–$C_5$-alkyl which is optionally substituted by halogen.

L in the general formulae preferably (and particularly preferably and very particularly preferably) represents oxygen.

M in the general formulae preferably (and particularly preferably and very particularly preferably) represents oxygen.

The definitions of radicals or illustrations mentioned above, are in general or in preferred ranges, can be combined with each other, that is to say that any combination between the individual preferred ranges is also possible. They apply to the end products and analogously to the precursors and intermediates.

Preferred according to the invention are those compounds of the general formula (I) in which there is a combination of the meanings mentioned :above as being preferred.

Particularly preferred according to the invention are those compounds of the general formula (I) in which there is a combination of the meanings mentioned above as being particularly preferred.

Very particularly preferred according to the invention are those compounds of the general formula (I) in which there is a combination of the meanings mentioned above as being very particularly preferred.

The 3-aryl-1,3-thiazines required as starting substances for carrying out process variants b), c), d), e), f), g) and h) according to the invention can be obtained by process variant a).

The acid halides of the formula (IV), carboxylic anhydrides of the formula (V), chloroformic esters or chloroformic thioesters of the formula (VI), chloromonothioformic esters or chlorodithioformic esters of the formula (VII), alkyl halides of the formula (VIII), sulphonyl chlorides of the formula (IX), phosphorus compounds of the formula (X), the compounds of the formulae (XI) and (XII) and the metal hydroxides and amines employed which are furthermore required as starting substances for carrying out process variants b), c), d), e), f), g) and h) according to the invention are generally known compounds of organic or inorganic chemistry.

The thioamide compounds of the formula (II) are also generally known compounds of organic chemistry.

Some of the compounds of the formula (III) are known (cf., for example, Org. Prep. Proced. Int. 7(4), 155–8, 1975 and DE 19 45 703). However, the compounds hitherto unknown can be prepared analogously in a simple manner by processes known in principle. For example, halogenocarbonyl ketenes of the formula (III) are obtained when arylmalonic acids of the formula (XIII)

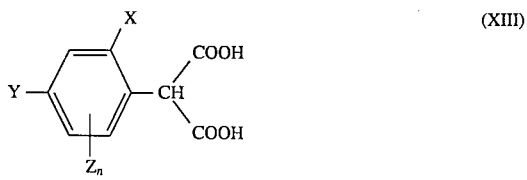

in which

X, Y, Z and n have the abovementioned meaning are reacted with acid halides such as, for example, thionyl chloride, phosphorus(V) chloride, phosphorus(III) chloride, oxalyl chloride, phosgene or thionyl bromide, if appropriate in the presence of catalysts such as, for example, diethylformamide, methylstearylformamide or triphenylphosphine.

The arylmalonic acids of the formula (XIII) are generally known compounds of organic chemistry (cf., for example, Organikum [Laboratory Practical in Organic Chemistry] VEB Deuscher Verlag der Wissenschaften, Berlin 1977, p. 517 et seq.).

Diluents which can be employed in process variant a) according to the invention are all inert organic solvents. The following can preferably be used: hydrocarbons, such as toluene and xylene, furthermore ethers, such as dibutyl ether, glycol dimethyl ether and diglycol dimethyl ether, moreover polar solvents, such as dimethyl sulphoxide, sulpholane, dimethylformamide and N-methyl-pyrrolidone.

Acid acceptors which can be used when carrying out process variant a) according to the invention are all customary acid acceptors.

The following can preferably be used: tertiary amines, such as triethylamine, pyridine, diazabicyclooctane (DABCO), diazabicycloundexzane (DBU), diazabicyclononene (DBN), Hünig base and N,N-dimethyl-aniline.

When carrying out process variant a) according to the invention, the reaction temperatures can be varied within a substantial range. The process is expediently carried out at temperatures between 0° C. and 250° C., preferably between 20° C. and 220° C.

Process variant a) according to the invention is expediently carded out under atmospheric pressure.

When carrying out process variant a) according to the invention, the reactants of the formulae (II) and (III) and, if appropriate, the acid acceptors are expediently employed in approximately equimolar amounts. However, it is also possible to use a large excess (up to 5 mol) of one or the other reactant.

Diluents which can be used in process variant b) α) according to the invention are, if the acid halides are use& all solvents which are inert to these compounds. The following can preferably be used: hydrocarbon, such as benzene, benzene, toluene, xylene and tetralin, furthermore halogenohydrocarbons, such as methylene chloride, chloroform, carbon tetrachloride, chlorobenzene and o-dichlorobezene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. If the acid halide is sufficiently stable to hydrolysis, the reaction can also be carried out in the presence of water.

If the corresponding carboxylic acid halides are used, then suitable acid-binding agents in the reaction by process variant b) α) according to the invention are all customary acid acceptors. The following can preferably be used: tertiary amines, such as triethylamine, pyridine, diazabicyclooctane (DABCO), diazabicycloundecane (DBU), diazabicyclononene (DBN), Hünig base and N,N-dimethylaniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

When carrying out process variant b) α) according to the invention, the reaction temperatures can again be varied within a substantial range. The process is expediently carried out at temperatures between –20° C. and +150° C., preferably between 0° C., and 100° C.

When carrying out process variant b) α) according to the invention, the starting substances of the formulae (I) and the carboxylic acid halide of the formula (V) are preferably used in approximately equivalent amounts. However, it is also possible to employ the carboxylic acid halide in a larger excess (up to 5 mol). Working-up is carried out by customary methods.

If, in process variant b) β) according to the invention, carboxylic anhydrides are employed as reactant of the formula (V), then diluents which can be used are preferably those which are also preferably suitable when acid halides are used. Besides, an excess of carboxylic anhydride employed can also simultaneously act as the diluent. The acid acceptors which can be employed are, again, the acid acceptors mentioned in process variant b) α).

When carboxylic anhydrides are used to carry out in process variant b) β) according to the invention, the reaction temperatures can again be varied within a substantial range. The process is expediently carried out at temperatures between −20° C. and +150° C., preferably between 0° C. and 100° C.

When carrying out the process according to the invention, the starting substances of the formula (I) and the carboxylic anhydride of the formula (V) are preferably used in approximately equivalent amounts. However, it is also possible to employ the carboxylic anhydride in a larger excess (up to 5 mol). Working-up is carried out by customary methods.

A procedure is expediently followed in which diluent and excess carboxylic anhydride as well as the carboxylic acid which forms are removed by distillation or by washing with an organic solvent or with water.

If, in process variant c), the corresponding chloroformic esters or chloroformic thioesters are used, then suitable acid-binding agents for the reaction are all customary acid acceptors.

The following can preferably be used: tertiary amines, such as triethylamine, pyridine, 1,4-diazabicyclo[2.2.2]octane (DABCO), 1,8-diazabicyclo[5.4.0]undec-7-ene (DBU), 1,5-diazabicyclo[4,3,0]non-5-ene (DBN), Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide or potassium hydroxide.

When using the chloroformic esters or chloroformic thioesters, then diluents which can be employed in process variant c) according to the invention are all solvents which are inert to these compounds. The following can preferably be used: hydrocarbons, such as benzene, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, in addition carboxylic esters, such as ethyl acetate, and also strongly polar solvents, such as dimethyl sulphoxide and sulpholane.

When using the chloroformic esters or chloroformic thioesters as carboxylic acid derivatives of the formula (VI), the reaction temperatures can be varied within a substantial range when carrying out process variant c). If the process is carried out in the presence of a diluent and of an acid-binding agent, the reaction temperatures are generally between −20° C. and +100° C., preferably between 0° C. and 50° C.

Process variant c) according to the invention is expediently carried out under atmospheric pressure.

When carrying out process variant c) according to the invention, the starting substances of the formula (I) and the corresponding chloroformic ester or chloroformic thioester of the formula (VI) are preferably used in approximately equivalent amounts. However, it is also possible to employ one or the other reactant in a larger excess (up to 2 mol). Working-up is then carried out by customary methods. A procedure is expediently followed in which salts which have precipitated are removed and the reaction mixture which remains is concentrated by stripping off the diluent.

In process variant d) α), approximately 1 mol of chloromonothioformic ester or chlorodithioformic ester of the formula (VII) is reacted per mole of starting compound of the formula (I) at 0° to 120° C., preferably at 20° to 60° C.

Suitable diluents which are optionally added are all inert polar organic solvents, such as ethers, amides, alcohols, sulphones and sulphoxides.

The following are preferably employed: dimethyl sulphoxide, tetrahydrofuran, dimethylformamide and dimethyl sulphide.

If, in a preferred embodiment, the enolate salt of the compound (I) is synthesized by adding strong deprotonating agents such as, for example, sodium hydride or potassium tertiary butylate, a further addition of acid-binding agents can be dispensed with.

If acid-binding agents are employed, then those which are suitable are customary inorganic or organic bases, with sodium hydroxide, sodium carbonate, potassium carbonate, pyridine and triethylamine being mentioned by way of example.

The reaction can be carried out under atmospheric pressure or under elevated pressure, it is preferably carded out under atmospheric pressure. Working-up is carried out by customary methods.

In process variant d) β), the equimolar amount or an excess of carbon disulphide is added per mole of starting compound of the formula (I). This process is preferably carried out at temperatures from 0° to 50° C., in particular 20° to 30° C.

Frequently, it is expedient first to prepare the corresponding salt from the compound of the formula (I) by adding a deprotonating agent (such as, for example, potassium tertiary butylate or sodium hydride). The compound (I) is reacted with carbon disulphide until formation of the intermediate is complete, for example after stirring at room texture for several hours.

The further reaction with the alkyl halide of the formula (VII) is preferably carried out at 0° to 70° C., in particular 20° to 50° C. At least the equimolar amount of alkyl halide is employed in this process.

The process is carried out under atmospheric pressure or under elevated pressure, preferably under atmospheric pressure.

Again, working-up is carded out by customary methods.

In process variant e), approximately 1 mol of sulphonyl chloride (IX) is reacted per mole of starting compound of the formula (I) at 0° to 150° C., preferably at 20° to 70° C.

Suitable diluents which are optionally added are all inert polar organic solvents, such as ethers, amides, nitriles, alcohols, sulphones, sulphoxides or halogenated hydrocarbons, such as methylene chloride.

The following are preferably employed: dimethyl sulphoxide, tetrahydrofuran and dimethylformamide.

If, in a preferred embodiment, the enolate salt of the compound (I) is synthesized by adding strong deprotonating agents (such as, for example, sodium hydride or potassium tertiary butylate), a further addition of acid-binding agents can be dispensed with.

If acid-binding agents are employed, then those which are suitable are customary inorganic or organic bases, with sodium hydroxide, sodium carbonate, potassium carbonate, pyridine and triethylamine being mentioned by way of example.

The reaction can be carried out under atmospheric pressure or under elevated pressure, it is preferably carried out under atmospheric pressure. Working-up is carried out by customary methods.

If appropriate, process variant e) can be carried out under phase transfer conditions (W. J. Spillane et al.; J. Chem. Soc., Perkin Trans I, (3) 677–9 (1982)). In this case, 0.3 to 1.5 mol of sulphonyl chloride (IX), preferably 0.5 mol, are reacted per mole of starting compound of the formula (I) at 0° to 150° C., preferably at 20° to 70° C.

Phase transfer catalysts which can be used are all quaternary ammonium salts, preferably tetrabutylammonium bromide and benzyltriethylammonium chloride. In this case, all unpolar inert solvents can act as organic solvents, and benzene and toluene are preferably employed.

In process variant f), 1 to 2, preferably 1 to 1.3, mol of the phosphorus compound of the formula (X) are reacted per 1 mol of the compound (I) at temperatures between −40° C. and 150° C., preferably between −10° and 110° C.

Suitable diluents which are optionally added are all inert polar organic solvents, such as ethers, amides, nitriles, alcohols, sulphides, sulphones, sulphoxides and the like.

The following are preferably employed: acetonitrile, dimethyl sulphoxide, tetrahydrofuran and dimethylformamide.

Suitable acid-binding agents which are optionally added are customary inorganic or organic bases, such as hydroxides or carbonates. Examples which may be mentioned are sodium hydroxide, sodium carbonate, potassium carbonate and pyridine.

The reaction can be called out under atmospheric pressure or under elevated pressure, it is preferably carried out under atmospheric pressure. Working-up is effected by customary methods of organic chemistry. The end products obtained are preferably purified by crystallization, by chromatographic purification or by so-called "incipient distillation", i.e. removal of the volatile components in vacuo.

Process variant g) is characterized in that compounds of the formula (I) are reacted with metal hydroxides or amines.

Diluents which can be employed in the process according to the invention are preferably ethers, such as tetrahydrofuran, dioxane or diethyl ether or else alcohols, such as methanol, ethanol and isopropanol, but also water. The process is preferably carried out under atmospheric pressure. The reaction temperatures are generally between −20° C. and 100° C., preferably between 0° C. and 50° C.

When carrying out process variant g) according to the invention, the starting substances are generally employed in approximately equimolar amounts. However, it is also possible to employ one or the other reactant in a larger excess (up to 2 mol). Expediently, a procedure is followed in which the reaction mixture is concentrated by stripping off the diluent.

In process variant h) α), approximately 1 mol of isocyanate of the formula (XI) is employed per mole of starting compound of the formula (I) at 0° to 100° C., preferably 20° to 50° C.

Suitable diluents which are optionally added are all inert organic solvents, such as ethers, amides, nitriles, sulphones or sulphoxides.

If appropriate, catalysts can be added to accelerate the reaction. Catalysts which can be employed very advantageously are organotin compounds such as, for example, dibutyltin dilaurate. The process is preferably carried out under atmospheric pressure.

In process variant h) β), approximately 1 mol of carbamoyl chloride or thiocarbamoyl chloride of the formula (XII) is reacted per mole of starting compound of the formula (I) at 0° to 150° C., preferably at 20° to 70° C.

Suitable diluents which are optionally added are all inert polar organic solvents such as ethers, amides, alcohols, sulphones and sulphoxides.

The following are preferably employed: dimethyl sulphoxide, tetrahydrofuran and dimethylformamide.

If, in a preferred embodiment, the enolate salt of the compound (I) is synthesized by adding strong deprotonating agents (such as, for example, sodium hydride or potassium tertiary butylate), a further addition of acid-binding agents can be dispensed with.

If acid-binding agents are employed, then those which are suitable are customary inorganic or organic bases, sodium hydroxide, sodium carbonate, potassium carbonate and pyridine being mentioned by way of example.

The reaction can be carried out under atmospheric pressure or under elevated pressure, it is preferably carried out under atmospheric pressure. Working-up is carried out by customary methods.

The compounds of the formula I according to the invention can be employed for pest control. Pests are undesirable animal pests, in particular insects, mites and nematodes, which damage plants or higher animals. However, the pests also include undesirable plants.

The active compounds according to the invention are suitable for combating animal pests, preferably arthropods, in particular insects, arachnids and nematodes, encountered in agriculture, in forestry, in the protection of stored products and of materials, and in the hygiene field, and have good plant tolerance and favorable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus,.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiums armatus.*

From the order of the Orthoptera, for example, *Blatta orientalis, Periplaneta americana, Leucophaea maderae, Blattella germanica, Acheta domesticus,* Gryllotalpa spp., *Locusta migratoria* migratorioides, *Melanoplus differentialis* and *Schistocerca gregaria.*

From the order of the Dermaptera, for example, *Forficula auricularia.*

From the order of the Isoptera, for example, Reticulitermes spp..

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea pp.

From the order of the Thysanoptera, for example, *Hercinothrips femoralis* and *Thrips tabaci.*

From the order of the Heteroptera for example, Eurygaster spp., *Dysdercus intermedius, Piesma quadrata, Cimex lectularius, Rhodnius prolixus* and Triatoma spp.

From the order of the Homoptera for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cineticeps, Lecanium comi, Saissetia oleae, Laodelphax striatellus, Nilaparvata lugens, Aonidiella aurantii, Aspidiotus hederae,* Pseudococcus spp. and Psylla spp.

From the order of the Lepidoptera for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Totrix viridana.*

From the order of the Coleoptera, for example, *Anobium punctatum, Rhizopertha dominica, Acanthoscelides obtecus, Hylotrupes bajulus, Agelastica alni, Leptinotarsa decemlineata, Phaedon cochleariae,* Diabrotica spp., *Psyllio des chrysocephala, Epilachna varivestis,* Atomaria spp., *Oryzaephilus surinamensis,* Anthonomus spp., Sitophilus spp., *Otiorrhynchus sulcatus, Cosmopalites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conodems spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Omithodorus spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp., The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidoms spp., Xiphinema spp. and Trichodoms spp..

In addition, the active compounds of the formula (I) according to, the invention also have a good fungicide activity and can be employed, for example, for combating plant diseases, such as, for example, against the pathogen causing rice blast disease (*Pyricularia oryzae*).

When used as insecticides, acaricides and nematicides, the active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, and others.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The compounds according to the invention are also particularly suitable for treating vegetative and generative propagation material, such as, for example, cereal seed, maize seed, vegetable seed and the like, or bulbs, cuttings and the like.

When used against hygiene pests and pests of stored produces, the active compounds are distinguished by an excellent residual action on wood and clay as well as a good stability to alkali on limed substrates.

The active compounds according to the invention can also be used as herbicides, preferably as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants. The compounds are suitable, depending on the concentration, for the total combating of weeds, for example on industrial terrain and rail tracks, and on paths and squares with and without tree plantings. Equally, the compounds can be employed for combating weeds in perennial cultures, for example afforestations, decorative tree plantings, orchards, vineyards, citrus groves, nut orchards, banana plantations, coffee plantations, tea plantations, robber plantations, oil palm plantations, cocoa plantations, soft fruit plantings and hopfields, in lawns, turf and pasture-land, and for the selective combating of weeds in annual cultures.

In particular, the compounds of the formula (I) according to the invention are suitable for selectively combating monocotyledon weeds in dicotyledon cultures, both by the pre-emergence and the post-emergence method.

The active compounds according to the invention, as such or their formulations, can also be used, for combating weeds, as a mixture with known herbicides, ready mixes or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chloropropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz; imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-methyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

To prepare the pesticides, the active compounds according to the invention can be converted to the customary formulations, such as solutions, emulsions, suspensions, powders, foams, pastes, granules, aerosols, natural and synthetic materials impregnated with active compound, very free capsules in polymeric substances and in coating compositions for seed, and formulations used with burning equipment, such as fumigating cartridges, fumigating cans, fumigating coils and the like, as well as ULV cold mist and warm mist formulations.

Depending on their particular physical and/or chemical properties, the active compounds can be converted to the customary formulations, such as solutions, emulsions, suspicions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or pararrins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, mommorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the me forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Preferably, the compositions according to the invention contain, besides at least one compound of the general formula (I) and, if appropriate, besides relevant extenders and auxiliaries, at least one surface-active substance.

While having low toxicity to warm-blooded species, the active compounds are also suitable for combating animal pests (ecto- and endoparasites), such as arthropods, preferably insects and arachnids (ectoparasites), Cestodes, Trematodes, Nematodes and Acantocephala (endoparasites), which occur in animal keeping and livestock breeding, and in domestic animals and in productive livestock, zoo animals, laboratory animals, experimental animals and pets. In this context, they are active against all or individual stages of development of the pests and against resistant and normally-sensitive pest species.

By combating the animal pests, it is intended to prevent diseases and their transmission, deaths and decreasing performance (for example in the production of meat, milk, wool, hides and eggs), so that more economical and simpler animal keeping is possible, or only made possible in the first place in certain areas, by using the active compounds.

The pests include:

From the order of the Anoplura, for example, Haematopinus spp., Linognathus spp., Solenopotes spp., Pediculus spp., Pthirus spp.;

from the order of the Mallophaga, for example, Trimenopon spp., Menopon spp., Eomenacanthus spp., Menacanthus spp., Trichodectes spp., Felicola spp., Damalinea spp., Bovicola spp;

from the order of the Diptera, for example, Crysops spp., Tabanus spp., Musca spp., Hydrotaea spp., Muscina spp., Haematobosca spp., Haematobia spp., Stomoxys spp., Fannia spp., Glossina spp., Lucilla spp., Calliphora spp., Auchmeromyia spp., Cordylobia spp., Cochliomyia spp., Chrysomia spp., Sarcophaga spp., Wohlfartia spp., Gasterophilus spp., Oesteromyia spp., Oedemagena spp., Hypoderma spp., Oestrus spp., Rhinoestrus spp., Melophagus spp., Hippobosca spp:

From the order of the Siphonaptera, for example Ctenocephalides spp., Echidnophaga spp., Ceratophyllus spp.

From the order of the Metastigmata, for example, Hyalomma spp., Rhipicephalus spp., Boophilus spp., Amblyomma spp., Haemophysalis spp., Dermacentor spp., Ixodes spp., Argas spp., Ornithodorus spp., Otobius spp.;

From the order of the Mesastigmata, for example, Dermanyssus spp., Ornithonyssus spp., Pneumonyssus spp..

From the order of the Prostigmata, for example, Cheyletiella spp., Psorergates spp., Myobia spp., Demodex spp., Neotrombicula spp.;

from the order of the Astigmata, for example, Acarus spp., Myocoptes spp., Psoroptes spp., Chorioptes spp., Otodectes spp., Sarcoptes spp., Notoedres spp., Knemidocoptes spp., Neoknemidocoptes spp., Lytodites spp., Laminosioptes spp..

The endoparasites include:

From the order of the Pseudophyllidea, for example: Diphyllobothrium spp., Spirometra spp., Schistocephalus spp., Ligula spp., Bothridium spp., Diphlogonoporus spp., From the order of the Cyclophyllidea, for example: Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp., From the subclass of the Monogenea, for example: Gyrodactylus spp., Dactylogyrus spp., Polystoma spp., From the subclass of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp-, Cotylophoron spp., Gigantocotyle spp., Fischoederius spp. Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonimus spp., From the order of the Enoplida, for example: Trichuris spp., Capillaria spp., Trichomosoides spp., Trichinella spp., From the order of the Rhabditia, for example: Micronema spp., Strongyloides spp., From the order of the Strongylida, for example: Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., protostrongylus spp., Neostrongylus spp., Cystocaulus spp., Pneumostrongylus spp., Spicocaulus spp., Elaphostrongylus spp. Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp., From the order of the Oxyurida, for example: Oxyuris spp., Enterobius spp., Passalurus spp., Syphacia spp., Aspiculuris spp., Heterakis spp..

From the order of the Spirurida, for example: Gnathostoma spp., Physaloptera spp., Thelazia spp., Gongylonema spp., Habronema spp., Parabronema spp., Draschia spp., Dracunculus spp..

From the order of the Filariida, for example: Stephanofilaria spp., Parafilaria spp., Setaria spp., Loa spp., Dirofilaria spp., Litomosoides spp., Brugia spp., Wuchereria spp., Onchocerca spp..

From the order of the Gigantorhynchida, for example Filicollis spp., Moniliformis spp., Macracanthorhynchus spp., Prosthenorchis spp., The productive livestock and breeding animals include mammals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chickens, geese, turkeys, ducks, freshwater and salt-water fish such as, for example, trout, carps, eels, reptiles, insects such as, for example, honeybee and silkworm.

Laboratory animals and experimental animals include mice, rats, guinea pigs, golden hamsters, dogs and cats.

Pets include dogs and cats.

Administration can be effected prophylactically as well as therapeutically. The active compounds are administered, directly or in the form of suitable preparations, enterally, parenterally, dermally, nasally, by environment treatment, or with the aid of active-compound-containing shaped articles such as, for example, strips, plates, bands, collars, ear marks, limb bands, marking devices.

The active compounds are administered enterally, for example orally, in the form of powders, suppositories, tablets, capsules, pastes, drinks, granules, drenches, boli, medicated feed or drinking water. Dermal administration is effected, for example, in the form of dipping, spraying, bathing, washing, pouring-on and spotting-on and dusting. Parenteral administration is effected, for example, in the form of an injection (intramuscular, subcutaneous, intravenous, intraperitoneal) or by implants.

Suitable preparations are:

Solutions such as injectable solutions, oral solutions, concentrates for oral administration after dilution, solutions for use on the skin or in body cavities, pour-on and spot-on formulations, gels;

Emulsions and suspension for oral or dermal administration and for injection; semi-solid preparations;

Formulations in which the active compound is incorporated in a cream base or in an oil-in-water or water-in-oil emulsion base;

Solid preparations such as powders, premixes or concentrates, granules, pellets, tablets, boli, capsules; aerosols and inhalants, shaped articles containing active compound.

Injectable solutions are administered intravenously, intramuscularly and subcutaneously.

Injectable solutions are prepared by dissolving the active compound in a suitable solvent and, if appropriate, adding additives such as solubilizers, acids, bases, buffer salts, antioxidants and preservatives. The solutions are sterile-filtered and drown off.

The following may be mentioned as solvents: physiologically acceptable solvents such as water, alcohols such as ethanol, butanol, benzyl alcohol, glycerol, hydrocarbons, propylene glycol, polyethylene glycols, N-methyl-pyrrolidone, and mixtures of these.

If appropriate, the active compounds can also be dissolved in physiologically acceptable vegetable or synthetic oils which are suitable for injection.

The following may be mentioned as solubilizers: solvents which enhance dissolution of the active compound in the main solvent, or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

Oral solutions are administered directly. Concentrates are administered orally after previously having been diluted to the administration concentration. Oral solutions and concentrates are prepared as described above in the case of the injectable solutions, it being possible to dispense with working under sterile conditions.

Solutions for use on the skin are applied dropwise, brushed on, robbed in, splashed on or sprayed on. These solutions are prepared as described above in the case of injectable solutions.

It may be advantageous to add thickeners during the preparation. Thickeners are: inorganic thickeners such as bentonites, colloidal silica, aluminium monostearate, organic thickeners such as cellulose derivatives, polyvinyl alcohols and their copolymers, acrylates and metacrylates.

Gels are applied to, or brushed on, the skin, or introduced into body cavities. Gels are prepared by treating solutions which have been prepared as described in the case of the injectable solutions with such an amount of thickener that a clear substance of cream-like consistency is formed. Thickeners employed are the thickeners indicated further above.

Pour-on and spot-on formulations are poured onto, or splashed onto, limited areas of the skin, the active compound either penetrating the skirt and acting systemically.

Pour-on and spot-on formulation are prepared by dissolving, suspending or emulsifying the active compound in suitable solvents or solvent mixtures which are tolerated by the skin. If appropriate, other adjuvants such as colourants, absorption accelerators, antioxidants, light stabilizers, and tackifiers are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methyl-pyrrolidone, 2,2-dimethyl-4-oxy-methylene- 1,3-dioxolane.

Colourants are all colourants which are licensed for me on animals and which can be dissolved or suspended.

Examples of absorption accelerators are DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Examples of light stabilizers are novantisolic acid.

Examples of adhesives are cellulose derivatives, starch derivatives, polyacrylates, natural polymers such as alginates, gelatine.

Emulsions can be administered orally, dermally or in the form of injections.

Emulsions are either of the water-in-oil type or of the oil-in-water type.

They are prepared by dissolving the active compound either in the hydrophobic or in the hydrophilic phase and homogenizing this phase with the solvent of the other phase, with the aid of suitable emulsifiers and, if appropriate, other adjuvants such as colourants, absorption accelerators, preservatives, antioxidants, light stabilizers and viscosity-increasing substances.

The following may be mentioned as the hydrophobic phase (oils): paraffin oils, silicone oils, natural vegetable oils such as sesame seed oil, almond oil, castor oil, synthetic triglycerides such as caprylic/capric acid bigylceride, triglyceride mixture with vegetable fatty acics of chain length $C_{8-12}$ or with other specifically selected natural fatty acids, partial glyceride mixtures of saturated or unsaturated fatty acids which may also contain hydroxyl groups, and mono- and diglycgrides of the $C_8/C_{10}$-fatty acids.

Fatty acid esters such as ethyl stearate, di-n-butyl adipate, hexyl laurate, dipropylene glycol pelargonate, esters of a branched fatty acid of medium chain length with sainted fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters, dibutyl phthalate, diisopropyl adipate, ester mixtures related to the latter, etc.

Fatty alcohols such as isotridecyl alcohol, 2-octyl dodecanol, cetylstearyl alcohol, oleyl alcohol.

Fatty acids such as, for example, oleic acid and its mixtures.

The following may be mentioned as hydrophilic phase: water, alcohol such as, for example, propylene glycol, glycerol, sorbitol and their mixtures.

The following may be mentioned as emulsifiers: non-ionic surfactants, for example polyoxyethylated castor oil, polyoxyethylated sorbitan monooleate, sorbitan monostearate, glycerol monostearate, polyoxyethyl stearate, alkylphenkol polyglycol ethers;

ampholytic surfactants such as disodium N-lauryl-β-iminodipropionate or lecithin;

anionic surfactants such as sodium lauryl sulphate, fatty alcohol ether sulphates, the monoethanolamine salt of mono/dialkyl polyglycol ether orthophosphoric esters;

cationic surfactants such as cetyltrimethylammonium chloride.

The following may be mentioned as other adjuvants: viscosity-increasing substances and substances which stabilise the emulsion, such as carboxymethylcellulose, methylcellulose and other cellulose and starch derivatives, polyacrylates, alginates, gelatine, gum arabic, polyvinylpyrrolidone, polyvinyl alcohol, copolymers of methyl vinyl ether and maleic anhydride, polyethylene glycols, waxes, colloidal silica, or mixtures of the substances mentioned.

Suspensions can be administered orally, dermally or in the form of injection. They are prepared by suspending the active compound in an excipient liquid, if appropriate with the addition of further adjuvants such as wetting agents, colourants, absorption accelerators, preservatives, antioxidants and light stabilizers.

Excipient liquids which may be mentioned are all homogenous solvents and solvent mixtures.

Wetting agents (dispersants) which may be mentioned are the surfactants indicated further above.

Further adjuvants which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of adjuvants, and the mixture is formulated as desired.

Excipients which may be mentioned are all physiologically acceptable solid inert substances. Suitable as such are inorganic and organic substances. Examples of inorganic substances are sodium chloride, carbonates such as calcium carbonate, hydrogen carbonates, aluminium oxides, silicas, clays, precipitated or colloidal silicon dioxide, and phosphates.

Examples of organic substances are sugars, cellulose, foods and animal feeds such as dried milk, carcass meals, cereal meals and coarse cereal meals and starches.

Adjuvants are preservatives, antioxidants and colourants which have already been indicated further above.

Other suitable adjuvants are the lubricants and glidants such as, for example, magnesium stearate, stearic acid, talc, bentonites, disintegrants such as starch or crosslinked polyvinylpyrrolidone, binders such as, for example, starch, gelatine or linear polyvinylpyrrolidone, and also dry binders such as microcrystalline cellulose.

The present invention thus also relates to the compounds of the general formula (I) for use as ecto- and endoparasiticides and to the use of the compounds of the general formula (I) for the preparation of a composition for combating ecto- and endoparasites.

In the preparations, the active compounds can also be present in the form of a mixture with synergists or with other active compounds which act against pathogenic endoparasites. Examples of such active compounds are L-2,3,5,6-tetrahydro- 6-phenylimidazothiazole, benzimidazole carbamates, praziquantel, pyrantel, febantel.

Ready-to-use preparations contain the active compound in concentrations of 10 ppm–20 percent by weight, preferably of 0.1–10 percent by weight.

Preparations which are diluted prior to administration contain the active compound in concentrations of 0.5–90 percent by weight, preferably 5 to 50 percent by weight.

In general, it has proved advantageous to administer amounts of approximately 1 to approximately 100 mg of active compound per kg of body weight per day, to achieve effective results.

The compounds according to the invention are preferably employed as anhropodicides and herbicides in plant protection and in the domestic and hygiene fields as well as in the protection of stored products, very particularly preferably in plant protection.

Unless otherwise indicated, all percentages are by weight.

The preparation of the compounds of the general formula (I) according to the invention will be illustrated by the preparation examples which follow and the biological activity by the biological examples which follow.

EXAMPLE 1

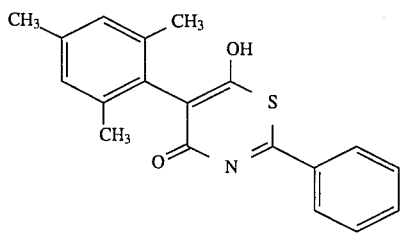

5.5 g (40 mmol) of thiobenazmide is added to 8.9 g (40 mmol) of chlorocarbonyl 2,4,6-trimethylphenyl ketene in 80 ml of absolute toluene with the exclusion of moisture at 20° C., and the mixture is heated for 6 hours at 50° C. The precipitate is separated off and recrystallized from ethyl acetate, and 5.1 g of 6-hydroxy-2-phenyl-5-(2,4,6-trimethylphenyl)-1,3-thiazin-4-one (yield: 39% of theory) are obtained. M.p.=240° to 242° C. $^1$H NMR (CD$_3$OD, TMS internal standard): δ=2.10 (s,6H), 2.26 (s,3H), 6.88 (s,2H), 7.56 (m,3H), 8.13 (m,2H).

EXAMPLE 2

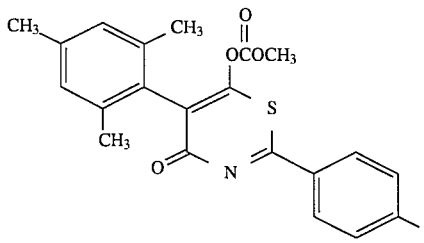

1.0 g (10 mmol) of triethylamine and then 0.94 g (10 mmol) of methyl chloroformate in 10 ml of ethyl acetate are added dropwise at 0° C. to 3.4 g (10 mmol) of 2-(4-fluorophenyl)-6-hydroxy-5-(2,4,6-trimethyl-phenyl)-1,3-thiazin-4-one in 50 ml of ethyl acetate. The mixture is stirred for 8 hours at 20° C. and filtered, the organic phase is washed using half-concentrated sodium chloride elusion and dried over sodium sulphate, and the solvent is evaporated in vacuo. The residue is chromatographed on silica gel (35 to 70 μm) using toluene/acetone (20:1 parts by volume). 3.1 g of 2-(4-fluorophenyl)-6-methoxycarbonyloxy-5-(2,4,6-trimethylphenyl)-1,3-thiazin-4-one are obtained (yield: 78% of theory). M.p.=129° to 131° C.

The 5-aryl-1,3-thiazine derivatives of the general formula (I) listed by way of their formulae in Tables 1 to 3 below are obtained analogously to the preparation examples and following the general information in the description of the preparation.

TABLE 1

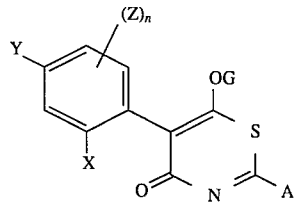

| Example | X | Y | $(Z)_n$ | G | A | M.p. (°C.) |
|---|---|---|---|---|---|---|
| 3 | CH$_3$ | CH$_3$ | 6-CH$_3$ | H | CH$_3$ | 155–159 |
| 4 | CH$_3$ | CH$_3$ | 6-CH$_3$ | H | CH(CH$_3$)$_2$ | 176–178 |
| 5 | CH$_3$ | CH$_3$ | 6-CH$_3$ | H | CH$_2$-2-Cl—C$_6$H$_4$ | 178–179 |
| 6 | CH$_3$ | CH$_3$ | 6-CH$_3$ | H | CH$_2$-3,4-Cl$_2$—C$_6$H$_3$ | 188–190 |
| 7 | CH$_3$ | CH$_3$ | 6-CH$_3$ | H | 4-F—C$_6$H$_4$ | 287–289 |
| 8 | CH$_3$ | CH$_3$ | 6-CH$_3$ | H | 3-Cl-4-F—C$_6$H$_3$ | 234–236 |
| 9 | CH$_3$ | CH$_3$ | 6-CH$_3$ | H | 2,6-Cl$_2$—C$_6$H$_3$ | 267–268 |
| 10 | CH$_3$ | CH$_3$ | 6-CH$_3$ | H | 4-CF$_3$—C$_6$H$_4$ | 246–248 |
| 11 | CH$_3$ | CH$_3$ | 6-CH$_3$ | H | 4-C(CH$_3$)$_3$—C$_6$H$_4$ | 264–266 |
| 12 | CH$_3$ | CH$_3$ | 6-CH$_3$ | H | 2-CH$_3$—C$_6$H$_4$ | 234–236 |
| 13 | CH$_3$ | CH$_3$ | 6-CH$_3$ | H | 3-CH$_3$—C$_6$H$_4$ | 218–220 |
| 14 | CH$_3$ | CH$_3$ | 6-CH$_3$ | H | 4-CH$_3$—C$_6$H$_4$ | 218–220 |
| 15 | CH$_3$ | CH$_3$ | 6-CH$_3$ | H | 2-F—C$_6$H$_4$ | 220–222 |
| 16 | CH$_3$ | CH$_3$ | 6-CH$_3$ | H | 3,4-Cl$_2$—C$_6$H$_3$ | 237–239 |
| 17 | CH$_3$ | CH$_3$ | 6-CH$_3$ | H | 2,4-Cl$_2$C$_6$H$_3$ | 240–242 |
| 18 | CH$_3$ | CH$_3$ | 6-CH$_3$ | H | 2,6-F$_2$—C$_6$H$_3$ | 243–245 |
| 19 | CH$_3$ | CH$_3$ | 6-CH$_3$ | H | 3,5-(CH$_3$O)$_2$—C$_6$H$_3$ | 217–219 |
| 20 | CH$_3$ | CH$_3$ | 6-CH$_3$ | H | 3-CF$_3$—C$_6$H$_4$ | 204 |
| 21 | Cl | H | H | H | 4-F—C$_6$H$_4$ | 239–240 |
| 22 | Cl | Cl | H | H | 4-F—C$_6$H$_4$ | 292–294 |

TABLE 1-continued

| Example | X | Y | (Z)ₙ | G | A | M.p. (°C.) |
|---|---|---|---|---|---|---|
| 23 | $CH_3$ | $CH_3$ | 6-$CH_3$ | H | 2-F-3-Cl-$C_6H_3$ | 241–243 |
| 24 | $CH_3$ | $CH_3$ | 6-$CH_3$ | H | (thiophene) | 255–258 |
| 25 | $CH_3$ | $CH_3$ | 6-$CH_3$ | H | $OC_6H_5$ | 211–213 |
| 26 | $CH_3$ | $CH_3$ | 6-$CH_3$ | H | $CON(CH_3)_2$ | 128–130 |
| 27 | $CH_3$ | $CH_3$ | 6-$CH_3$ | $COCH_3$ | 2,4-$Cl_2$-$C_6H_3$ | 145–148 |
| 28 | $CH_3$ | $CH_3$ | 6-$CH_3$ | $CO_2CH_3$ | 2,6-$F_2$-$C_6H_3$ | 189–191 |
| 29 | $CH_3$ | $CH_3$ | 6-$CH_3$ | $COCH_3$ | 4-F-$C_6H_4$ | 128–130 |
| 30 | $CH_3$ | $CH_3$ | 6-$CH_3$ | $COC(CH_3)_3$ | 4-F-$C_6H_4$ | 183 |
| 31 | $CH_3$ | $CH_3$ | 6-$CH_3$ | $CO_2C_2H_5$ | 2,4-$Cl_2$-$C_6H_3$ | 150–151 |
| 32 | $CH_3$ | $CH_3$ | 6-$CH_3$ | H | $OCH_2CCl_3$ | 209–211 |
| 33 | $CH_3$ | $CH_3$ | 6-$CH_3$ | H | O-4-Cl-$C_6H_4$ | 235–236 |
| 34 | $CH_3$ | $CH_3$ | 6-$CH_3$ | H | O-2,6-$(CH_3)_2$-$C_6H_3$ | 178–180 |
| 35 | $CH_3$ | $CH_3$ | 6-$CH_3$ | H | $SCH_2$-(thiophene) | 195–196 |
| 36 | $CH_3$ | $CH_3$ | 6-$CH_3$ | H | $SCH_2C_6H_5$ | 162–165 |
| 37 | $CH_3$ | $CH_3$ | 6-$CH_3$ | H | CO-3,4-$Cl_2C_6H_3$ | 206–208 |
| 38 | $CH_3$ | $CH_3$ | 6-$CH_3$ | H | CO-4-Cl-$C_6H_4$ | 207–208 |
| 39 | $CH_3$ | $CH_3$ | 6-$CH_3$ | H | CO-$C_6H_5$ | 183–186 |
| 40 | $CH_3$ | $CH_3$ | 6-$CH_3$ | H | 4-$CH_3$S-$C_6H_4$ | 240–242 |
| 41 | $CH_3$ | $CH_3$ | 6-$CH_3$ | H | 4-$NO_2$-$C_6H_4$ | 261–263 |
| 42 | $CH_3$ | $CH_3$ | 6-$CH_3$ | H | 4-Cl-$C_6H_4$ | 278–280 |

Preparation of the starting compounds of the formula (III)

EXAMPLE (III-1)

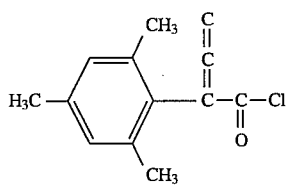

444.5 g (2 mol) of mesitylmalonic acid are suspended in 1000 ml of methylcyclohexane at 75–80° C., and 714 g (6 mol) of thionyl chloride are added dropwise in the course of 3 hours. The mixture is then slowly heated further, and stirring is continued for 8 hours at a bath temperature of 110°–120° C. with reflux cooling.

Excess thionyl chloride is distilled off together with the solvent at 10 mbar and a bath temperature of up to 80° C., and, after cooling, the residue is diluted with 3 times the amount of petroleum ether and filtered, the filtrate is concentrated, and the concentrate is distilled.

373 g (84% of theory) of mesityl chlorocarbonyl ketene of boiling point 96° /0.45 mbar are obtained.

The remaining starting compounds of the formula (III) can be prepared analogously to Example (III-1) and taking into account the information given in the description of the processes according to the invention.

Example A

Phaedon larvae test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica olemcea*) are treated by being dipped into the preparation of the active compound of the desired concentration and are infested with mustard beetle larvae (*Phaedon cochleariae*), while the leaves are still moist.

After the desired period of time, the destruction in % is determined. 100% means that all the beetle larvae have been killed; 0% means that none of the beetle larvae have been killed.

In this test, a destruction of 100% was shown after 7 days for example by the compounds of Preparation Examples 1, 7, 10, 29 and 2 at an exemplary concentration of 0.1%.

Example B

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica olemcea*) are treated by being dipped into the preparation of active compound of the desired concentration and are infested with caterpillars of the diamond-back moth (*Plutella maculipennis*) while the leaves are still moist.

After the desired period of time, the destruction in % is determined. 100% means that all the caterpillars have been killed; 0% means that none of the caterpillars have been killed.

In this test, a destruction of 100% was shown after 7 days for example by the compounds of Preparation Examples 2, 7, 10, 29 and 30 at an exemplary concentration active compound of 0.1%.

Example C

Nephotettix test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with larvae of the green rice leafhopper (*Nephotettix cincticeps*) while the leaves are still moist.

After the desired period of time, the destruction in % is determined. 100% means that all the leafhoppers have been killed; 0% means that none of the leafhoppers have been killed.

In this test, a destruction of 100% was shown alter 6 days for example by the compounds of Preparation Examples 2, 7, 12, 15, 29 and 30 at an exemplary concentration of active compound 0.1%.

Example D

*Heliothis virescens* test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) are treated by being dipped into the preparation of active compound of the desired concentration and are infested with caterpillars of the tobacco budworm (*Heliothis virescens*) while the leaves are still moist.

After the desired period of time, the destruction in % is determined. 100% means that all the leafhoppers have been killed; 0% means that none of the leafhoppers have been killed.

In this test, a good activity was shown, for example, by the compounds of the Preparation Examples.

Example E

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, an exemplary application rate of 500 to 1,000 g/ha gave the following results while being well to very well tolerated by beet:

| Plant | % Activity | Compound of Preparation Example No. |
|---|---|---|
| Alopecurus | 95 | 1, 7, 29 |
| Cynodon | 100 | 1, 7, 29 |
| Echinochloa | 90–100 | 1, 7, 29 |
| Lolium | 95–100 | 1, 7, 29 |
| Poa | 80–100 | 1, 7, 29 |

We claim:

1. A substituted 5-aryl-1,3-diazine of the formula $$\text{(I)}$$

in which

A represents $C_1$–$C_{10}$-alkyl, $C_3$–$C_{10}$-alkenyl, $C_3$–$C_{10}$-alkinyl, and $C_3$–$C_{10}$-cycloalkyl which are optionally substituted by halogen; or represents phenyl, naphthyl, hetaryl, phenyl-$C_1$–$C_6$-alkyl and hetaryl-$C_1$–$C_6$-alkyl which are optionally substituted by halogen, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy or CN; or represents $C_1$–$C_{10}$-alkoxy, $C_3$–$C_{10}$-alkenyloxy, $C_3$–$C_{10}$-alkinyl-oxy, and $C_3$–$C_{10}$-cycloalkoxy which are optionally substituted by halogen; or represents phenyloxy, naphthyloxy, hetaryloxy, phenyl-$C_1$–$C_6$-alkoxy and hetaryl-$C_1$–$C_6$-alkoxy which are optionally substituted by halogen, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy or CN; or represents $C_1$–$C_{10}$-alkylthio, $C_3$–$C_{10}$-alkenylthio, $C_3$–$C_{10}$-alkinylthio and $C_3$–$C_{10}$-cycloalkylthio which are optionally substituted by halogen; or represents phenylthio, naphthylthio, hetarylthio, phenyl-$C_1$–$C_6$-alkylthio and hetaryl-$C_1$–$C_6$-alkylthio which are optionally substituted by halogen, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy or CN; or represents the groups $COR^1$, $CSR^1$, $CO_2R^1$,

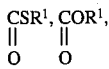

$CS_2R^1$, CN, $CONR^1R^2$ and $CSNR^1R^2$, where $R^1$ and $R^2$ independently of one another represent $C_1$–$C_{10}$-alkyl and $C_3$–$C_{10}$-alkenyl which are optionally substituted by halogen; or represent phenyl, naphthyl, hetaryl, phenyl-$C_1$–$C_6$-alkyl and hetaryl-$C_1$–$C_6$-alkyl which are optionally substituted by halogen, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy or CN; or $R^1$ and $R^2$ together represent $C_2$–$C_7$-alkylene group or represents —$(CH_2)_2$—O—$(CH_2)_2$—, —$(CH_2)_2$—S—$(CH_2)_2$—, —O—CO—$CH_2$—, X represents halogen, $C_1$–$C_6$-alkyl or $C_1$–$C_6$-alkoxy;

Y represents hydrogen, halogen, $C_1$–$C_6$-alkyl, halogen-$C_1$–$C_6$-alkyl or $C_1$–$C_6$-alkoxy;

Z represents hydrogen, halogen, $C_1$–$C_6$-alkyl or $C_1$–$C_6$-alkoxy;

n represents an integer 1, 2 or 3; and

G represents hydrogen, a cation of an alkaline earth metal or alkali metal, an ammonium ion or a group —$COR^3$,

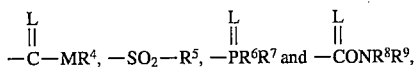

in which $R^3$ represents optionally halogen substituted radical selected from the group consisting $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, $C_1$–$C_8$-polyalkoxy-$C_1$–$C_8$-alkyl and $C_3$–$C_8$-cycloalkyl; or represents phenyl which is optionally substituted by halogen, nitro, $C_1$–$C_6$-alkyl, $C_1$–$C_6$-alkoxy, $C_1$–$C_6$-halogenoalkyl or $C_1$–$C_6$-halogenoalkoxy; or represents phenyl-$C_1$–$C_6$-alkyl which is optionally substituted by halogen, $C_1$–$C_6$-alkyl, $C_1$–$C_6$-alkoxy, $C_1$–$C_6$-halogenoalkyl or $C_1$–$C_6$-halogenoalkoxy; halogenoalkoxy; or represents hetaryl which is optionally substituted by halogen or $C_1$–$C_6$-alkyl; or represents phenoxy-$C_1$–$C_6$-alkyl which is optionally substituted by halogen or $C_1$–$C_6$-alkyl, or represents hetaryloxy-$C_1$–$C_6$-alkyl which is optionally substituted by halogen, amino or $C_1$–$C_6$-alkyl;

$R^4$ represents optionally substituted radical from the group consisting of $C_1$–$C_{20}$-alkyl, $C_2$–$C_{20}$-alkenyl, $C_1$–$C_8$-alkoxy-$C_1$–$C_8$-alkyl and $C_1$–$C_8$-polyalkoxy-$C_1$–$C_8$-alkyl which are optionally substituted by halogen; or represents radicals from the group consisting of phenyl and benzyl which are optionally substituted by halogen, nitro, $C_1$–$C_6$-alkyl, $C_1$–$C_6$-alkoxy or $C_1$–$C_6$-halogenoalkyl;

$R^5$, $R^6$ and $R^7$ independently of one another represent $C_1$–$C_8$-alkyl, $C_1$–$C_8$-alkoxy, $C_1$–$C_8$-alkylthio, $C_1$–$C_8$-alkylamino, di($C_1$–$C_8$)-alkylamino, $C_2$–$C_5$-alkenylthio, $C_2$–$C_5$-alkinylthio and $C_3$–$C_7$-cycloalkylthio which are optionally substituted by halogen; or represent a radical selected from the group consisting of phenyl, phenyloxy and phenylthio which are optionally substituted by halogen, nitro, cyano, $C_1$–$C_4$-alkoxy, $C_1$–$C_4$-alkylthio, $C_1$–$C_4$-halogenoalkoxy, $C_1$–$C_4$-halogenoalkylthio, $C_1$–$C_4$-alkyl or $C_1$–$C_4$-halogenoalkyl;

$R^8$ and $R^9$ independently of one another represent hydrogen or radical selected from the group consisting of $C_1$–$C_{20}$-alkyl, $C_1$–$C_{20}$-alkoxy, $C_3$–$C_{10}$-cycloalkyl, $C_2$–$C_8$-alkenyl and $C_1$–$C_8$-alkoxy-$C_1$–$C_8$-alkyl which are optionally substituted by halogen; or represent radicals from the group consisting of phenyl and benzyl which are optionally substituted by halogen, $C_1$–$C_{20}$-alkyl, $C_1$–$C_{20}$-halogenoalkyl or $C_1$–$C_{20}$-alkoxy; or together form an optionally substituted $C_2$–$C_6$-alkylene group or together form —$(CH_2)_2$—O—$(CH_2)_2$—, —$(CH_2)_2$—S—$(CH_2)_2$—, —O—CO—$CH_2$—;

L represents oxygen or sulphur; and

M represents oxygen or sulphur;

wherein the heteroaryl moieties are selected from the group consisting of pyrryl, furyl, thienyl, thiazolyl, pyridyl, pyrazolyl, and pyrimidinyl.

2. The compound according to claim 1, in which

A represents $C_1$–$C_8$-alkyl, $C_3$–$C_8$-alkenyl, $C_3$–$C_8$-alkynyl, and $C_3$–$C_8$-cyclo-alkyl which are optionally substituted by halogen; or represents phenyl, naphthyl, hetaryl, hetaryl-$C_1$–$C_4$ and phenyl-$C_1$–$C_4$-alkyl which are optionally substituted by halogen, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy or CN; or represents $C_1$–$C_6$-alkoxy, $C_3$–$C_{10}$-alkenyloxy, $C_3$–$C_6$-alkynyloxy, and $C_3$–$C_6$-cycloalkoxy which are optionally substituted by halogen; or represents phenyloxy, naphthyloxy, phenyl-$C_1$–$C_2$-alkoxy, thienyloxy, furyloxy, thiazolyloxy, pyridyloxy, and pyrazolyloxy which are optionally substituted by halogen, nitro, $C_1$–$C_4$-alkyl, $C_1$–$C_4$-alkoxy, $C_1$–$C_4$-alkythio, $C_1$–$C_4$-halogenoalkyl, $C_1$–$C_4$-halogenoalkoxy or CN; or represents $C_1$–$C_6$-alkylthio, $C_3$–$C_6$-alkenylthio, $C_3$–$C_1$-alkinylthio and $C_3$–$C_6$-cycloalkylthio which are optionally substituted by halogen; or represents phenylthio, naphthylthio, phenyl-$C_1$–$C_2$-alkylthio, thienylthio, thienyl-$C_1$–$C_2$-alkylthio, furylthio, thiazolylthio, pyridylthio and pyrazolylthio which are optionally substituted by halogen, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenalkoxy or CN; or represents the groups $COR^1$, $CSR^1$, $CO_2R^1$

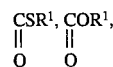

$CS_2R^1$, CN, $CONR^1R^2$ and $CSNR^1R^2$, where $R^1$ and $R^2$ independently of one another represent radicals selected from the group consisting of $C_1$–$C_6$-alkyl and $C_3$–$C_6$-alkenyl which are optionally substituted by halogen; or represent phenyl which is optionally substituted by halogen, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy or CN;

X represents halogen, $C_1$–$C_4$-alkyl or $C_1$–$C_4$-alkoxy;

Y represents hydrogen, halogen, $C_1$–$C_4$-alkyl, $C_1$–$C_4$-alkoxy, $C_1$–$C_4$-halogenoalkyl;

Z represents hydrogen, halogen, $C_1$–$C_4$-alkyl, or $C_1$–$C_4$-alkoxy;

$R^3$ represents optionally halogen-substituted radicals from the group consisting of $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl, $C_1$–$C_6$-polyalkoxy-$C_1$–$C_6$-alkyl and $C_3$–$C_7$-cycloalkyl; or represents phenyl which is optionally substituted by halogen, nitro, $C_1$–$C_4$-alkyl, $C_1$–$C_4$-alkoxy, $C_1$–$C_3$-halogenoalkyl or $C_1$–$C_3$-halogenoalkoxy; or represents phenyl-$C_1$–$C_4$-alkyl which is optionally substituted by halogen, $C_1$–$C_4$-alkyl, $C_1$–$C_4$- alkoxy, $C_1$–$C_3$-halogenoalkyl or $C_1$–$C_3$-halogenoalkoxy; or represents hetaryl which is optionally substituted by halogen or $C_1$–$C_6$-alkyl; or represents phenoxy-$C_1$–$C_5$-alkyl which is optionally substituted by halogen or $C_1$–$C_4$-alkyl; or represents hetaryloxy-$C_1$–$C_5$-alkyl which is optionally substituted by halogen, amino or $C_1$–$C_4$-alkyl;

$R^4$ represents a radical selected from the group consisting of $C_1$–$C_{16}$-alkyl, $C_2$–$C_{16}$-alkenyl, $C_1$–$C_6$-alkoxy-$C_1$–$C_6$-alkyl and $C_1$–$C_6$-polyalkoxy-$C_1$–$C_6$-alkyl which are optionally substituted by halogen; or represents a radical selected from the group consisting of phenyl and benzyl which are optionally substituted by halogen, nitro, $C_1$–$C_4$-alkyl, $C_1$–$C_3$-alkoxy or $C_1$–$C_3$-halogenoalkyl;

$R^5$, $R^6$, and $R^7$ represent radicals selected from the group consisting of $C_1$–$C_6$-alkyl, $C_1$–$C_6$-alkoxy, $C_1$–$C_6$-alkylthio, $C_1$–$C_6$-alkylthio, $C_1$–$C_6$-alkylamino, di($C_1$–$C_6$)-alkylamino, $C_2$–$C_6$-alkenylthio, $C_2$–$C_6$-alkinylthio and $C_3$–$C_6$-cycloalkylthio which are optionally substituted by halogen; or represent radicals selected from the group consisting of phenyl, phenyloxy and phenylthio which are optionally substituted by halogen, nitro, cyano, $C_1$–$C_3$-alkoxy, $C_1$–$C_3$-alkylthio, $C_1$–$C_3$-halogenoalkoxy, $C_1$–$C_3$-halogenoalkylthio, $C_1$–$C_3$-alkyl or $C_1$–$C_3$-halogenoalkyl;

$R^8$ and $R^9$ independently represent hydrogen, or represent a radical selected from the group consisting of $C_1$–$C_{16}$-alkyl, $C_1$–$C_{16}$-alkoxy, $C_3$–$C_{16}$-cycloalkyl, $C_2$–$C_6$-alkenyl or $C_1$–$C_6$-alkoxy-$C_1$–$C_6$-alkyl which are optionally substituted by halogen; or represent radicals from the group consisting of phenyl and benzyl which are optionally substituted by halogen, $C_1$–$C_6$-alkyl, $C_1$–$C_6$-halogenoalkyl or $C_1$–$C_6$-alkoxy wherein the hetaryl moieties are selected from the group consisting of pyrryl, furyl, thienyl, thiazolyl, pyridyl, pyrazolyl, and pyrimidinyl.

3. The compound according to claim 1, which

A represents phenyl, phenoxy and phenylthio which are optionally substituted by halogen;

X represents fluorine, chlorine, bromine, methyl, ethyl, n- and i-propyl, methoxy or ethoxy, Y represents hydrogen, fluorine, chlorine, bromine, $C_1$–$C_4$-alkyl or trifluoromethyl;

Z represents hydrogen, fluorine, chlorine, bromine, $C_1$–$C_4$-alkyl, methoxy or ethoxy;

n represents 1;

G represents hydrogen, —$COR^3$ or

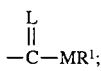

$R^3$ represents a radical selected from the group consisting of $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, $C_1$-polyalkoxy-$C_1$–$C_6$-alkyl and $C_3$–$C_6$-cycloalkyl, which are optionally substituted by fluorine or chlorine; or represents phenyl which is optionally substituted by fluorine, chlorine, bromine, nitro, $C_1$–$C_3$-alkyl, methoxy, ethoxy, trifluoromethyl or trifluoromethoxy; or represents phenyl-$C_1$–$C_3$-alkyl which is optionally substituted by fluorine, chlorine, bromine, $C_1$–$C_3$-alkyl, methoxy, ethoxy, trifluoromethyl or trifluoromethoxy; or represents a radical selected from the group consisting of pyridyl, pyrimidyl, thiazolyl and pyrazolyl which are optionally substituted by fluorine, chlorine, bromine, methyl or ethyl; or represents phenoxy-$C_1$–$C_4$-alkyl which is optionally substituted by fluorine, chlorine, methyl or ethyl; or represents radical selected from the group consisting of pyridyloxy-$C_1$–$C_4$-alkyl, pyrimidyloxy-$C_1$–$C_4$-alkyl and thiazolyloxy-$C_1$–$C_4$-alkyl which are optionally substituted by fluorine, chlorine, amino, methyl or ethyl;

$R^4$ represents a radical selected from the group consisting of $C_1$–$C_{14}$-alkyl, $C_2$–$C_{14}$-alkenyl, $C_1$–$C_4$-alkoxy-$C_1$–$C_6$-alkyl and $C_1$–$C_4$-polyalkoxy-$C_1$–$C_6$-alkyl which are optionally substituted by fluorine or chlorine, or represents a radical selected from the group consisting of phenyl and benzyl which are optionally substituted by fluorine, chlorine, nitro, $C_1$–$C_3$-alkyl, methoxy, ethoxy or trifluoromethyl;

$R^5$, $R^6$ and $R^7$ independently of one another represent a radical selected from the group consisting of $C_1$–$C_4$-alkyl, $C_1$–$C_4$-alkoxy, $C_1$–$C_4$-alkylthio, $C_1$–$C_4$-alkylamino or di($C_1$–$C_4$)-alkylamino which are optionally substituted by fluorine or chlorine; or represent radicals selected from the group consisting of phenyl, phenyloxy and phenylthio which are optionally substituted by halogen, nitro, cyano, $C_1$–$C_2$-alkoxy, $C_1$–$C_2$-alkylthio, $C_1$–$C_2$-fluoroalkoxy, $C_1$–$C_2$-chloroalkoxy, $C_1$–$C_2$-fluoroalkylthio, $C_1$–$C_2$-chloroalkylthio and $C_1$–$C_3$-alkyl;

$R^8$ and $R^9$ independently of one another represent hydrogen, or represent a radical selected from the group consisting of $C_1$–$C_{10}$-alkyl, $C_1$–$C_{10}$-alkoxy and $C_1$–$C_4$-alkoxy-$C_1$–$C_4$-alkyl which are optionally substituted by halogen, or represent radicals selected from the group consisting of phenyl and benzyl which are optionally substituted by halogen, $C_1$–$C_4$-alkyl, $C_1$–$C_4$-halogenoalkyl or $C_1$–$C_4$-alkoxy;

L represent oxygen;

M represents oxygen.

4. A process for the preparation of a substituted 5-aryl-1,3-thiazine derivative of the formula

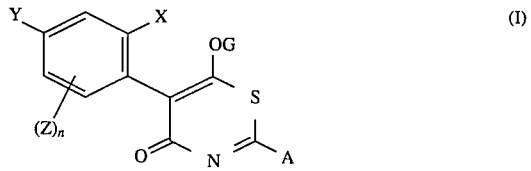

in which

A represents $C_1$–$C_{10}$-alkyl, $C_3$–$C_{10}$-alkenyl, $C_3$–$C_{10}$-alkinyl, and $C_3$–$C_{10}$-cycloalkyl which are optionally substituted by halogen; or represents phenyl, naphthyl, hetaryl, phenyl-$C_1$–$C_6$-alkyl and hetaryl-$C_1$–$C_6$-alkyl which are optionally substituted by halogen, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy or CN; or represents $C_1$–$C_{10}$-alkoxy, $C_3$–$C_{10}$-alkenyloxy, $C_3$–$C_{10}$-alkinyl-oxy, and $C_3$–$C_{10}$-cycloalkoxy which are optionally substituted by halogen; or represents phenyloxy, naphthyloxy, hetaryloxy, phenyl-$C_1$–$C_6$-alkoxy and hetaryl-$C_1$–$C_6$-alkoxy which are optionally substituted by halogen, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy or CN; or represents $C_1$–$C_{10}$-alkylthio, $C_3$–$C_{10}$-alkenylthio, $C_3$–$C_{10}$-alkinylthio and $C_3$–$C_{10}$-cycloalkylthio which are optionally substituted by halogen; or represents phenylthio, naphthylthio, hetarylthio, phenyl-$C_1$–$C_6$-alkylthio and hetaryl- $C_1$–$C_6$-alkylthio which are optionally substituted by halogen, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy or CN; or represents the groups $COR^1$, $CSR^1$, $CO_2R^1$, $$\underset{O}{\overset{CSR^1,}{\overset{\|}{}}} \underset{S}{\overset{COR^1,}{\overset{\|}{}}}$$

$CS_2R^1$, CN, $CONR^1R^2$, and $CSNR^1R^2$, where $R^1$ and $R^2$ independently of one another represent $C_1$–$C_{10}$-alkyl and $C_3$–$C_{10}$-alkenyl which are optionally substituted by halogen; or represent phenyl, naphthyl, hetaryl, phenyl-$C_1$–$C_6$-alkyl and hetaryl-$C_1$–$C_6$-alkyl which are optionally substituted by halogen, nitro, $C_1$–$C_8$-alkyl, $C_1$–$C_8$-alkoxy, $C_1$–$C_8$-alkylthio, $C_1$–$C_8$-halogenoalkyl, $C_1$–$C_8$-halogenoalkoxy or CN; or $R^1$ and $R^2$ together represent $C_2$–$C_7$-alkylene group or represents —$(CH_2)_2$—O—$(CH_2)_2$—, —$(CH_2)_2$—S—$(CH_2)_2$—, —O—CO—$CH_2$—, X represents halogen, $C_1$–$C_6$-alkyl or $C_1$–$C_6$-alkoxy;

Y represents hydrogen, halogen, $C_1$–$C_6$-alkyl, halogen-$C_1$–$C_6$-alkyl or $C_1$–$C_6$-alkoxy;

Z represents hydrogen, halogen, $C_1$–$C_6$-alkyl or $C_1$–$C_6$-alkoxy;

n represents an integer 1, 2 or 3; and

G represents hydrogen, a cation of an alkaline earth metal or alkali metal, an ammonium ion or a group —$COR^3$, $$-\overset{\overset{L}{\|}}{C}-MR^4, -SO_2-R^5, -\overset{\overset{L}{\|}}{P}R^6R^7 \text{ and } -\overset{\overset{L}{\|}}{C}ONR^8R^9,$$

in which $R^3$ represents optionally halogen substituted radical selected from the group consisting $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, $C_1$–$C_8$-polyalkoxy-$C_1$–$C_8$-alkyl and $C_3$–$C_8$-cycloalkyl; or represents phenyl which is optionally substituted by halogen, nitro, $C_1$–$C_6$-alkyl, $C_1$–$C_6$-alkoxy, $C_1$–$C_6$-halogenoalkyl or $C_1$–$C_6$-halogenoalkoxy; or represents phenyl-$C_1$–$C_6$-alkyl which is optionally substituted by halogen, $C_1$–$C_6$-alkyl, $C_1$–$C_6$-alkoxy, $C_1$–$C_6$-halogenoalkyl or $C_1$–$C_6$-halogenoalkoxy; or represents hetaryl which is optionally substituted by halogen or $C_1$–$C_6$-alkyl; or represents phenoxy-$C_1$–$C_6$-alkyl which is optionally substituted by halogen or $C_1$–$C_6$-alkyl, or represents hetaryloxy-$C_1$–$C_6$-alkyl which is optionally substituted by halogen, amino or $C_1$–$C_6$-alkyl;

$R^4$ represents optionally substituted radical from the group consisting of $C_1$–$C_{20}$-alkyl, $C_2$–$C_{20}$-alkenyl, $C_1$–$C_8$-alkoxy-$C_1$–$C_8$-alkyl and $C_1$–$C_8$-polyalkoxy-$C_1$–$C_8$-alkyl which are optionally substituted by halogen; or represents radicals from the group consisting of phenyl and benzyl which are optionally substituted by halogen, nitro, $C_1$–$C_6$-alkyl, $C_1$–$C_6$-alkoxy or $C_1$–$C_6$-halogenoalkyl;

$R^5$, $R^6$ and $R^7$ independently of one another represent $C_1$–$C_8$-alkyl, $C_1$–$C_8$-alkoxy, $C_1$–$C_8$-alkylthio, $C_1$–$C_8$-alkylamino, di($C_1$–$C_8$)-alkylamino, $C_2$–$C_5$-alkenylthio, $C_2$–$C_5$-alkinylthio and $C_3$–$C_7$-cycloalkylthio which are optionally substituted by halogen; or represent a radical selected from the group consisting of phenyl, phenyloxy and phenylthio which are optionally substituted by halogen, nitro, cyano, $C_1$–$C_4$-alkoxy, $C_1$–$C_4$-alkylthio, $C_1$–$C_4$-halogenoalkoxy, $C_1$–$C_4$-halogenoalkylthio, $C_1$–$C_4$-alkyl or $C_1$–$C_4$-halogenoalkyl;

$R^8$ and $R^9$ independently of one another represent hydrogen or radical selected from the group consisting of $C_1$–$C_{20}$-alkyl, $C_1$–$C_{20}$-alkoxy, $C_3$–$C_{10}$-cycloalkyl, $C_2$–$C_8$-alkenyl and $C_1$–$C_8$-alkoxy-$C_1$–$C_8$-alkyl which are optionally substituted by halogen; or represent radicals from the group consisting of phenyl and benzyl which are optionally substituted by halogen, $C_1$–$C_{20}$-alkyl, $C_1$–$C_{20}$-halogenoalkyl or $C_1$–$C_{20}$-alkoxy; or together form an optionally substituted $C_2$–$C_6$-alkylene group or together form —$(CH_2)_2$—O—$(CH_2)_2$—, —$(CH_2)_2$—S—$(CH_2)_2$—, —O—CO—$CH_2$—;

L represents oxygen or sulphur; and

M represents oxygen or sulphur;

which comprises reacting a thiomide of the formula $$H_2N-\overset{\overset{S}{\|}}{C}-A \quad \text{(II)}$$

in which

A has the abovementioned meaning, with a ketenic acid halide of the formula

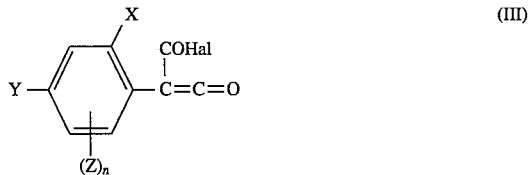

in which

X, Y, Z and n have the abovementioned meanings and

Hal represents hydrogen in the presence of a diluent, and optionally in the presence of an acid acceptor.

5. An arthropodicidal nematicidal, herbicidal or fungicidal composition comprising an arthropodicidally nematicidally herbicidally or fungicidally effective amount of a compound according to claim 1 and a diluent.

6. A method of combatting an arthropod, nematode or fungus which comprises applying to said arthropod, nematode or fungus an arthropodically nematicidally, or fungicidally effective amount of a compound according to claim 1.

7. The method according to claim 6, wherein the insects or nematodes are ectoparasites or endoparasites.

8. A method of controlling unwanted plant growth which comprises applying a herbicidally effective amount of a compound according to claim 1 to said plant or to its habitat.

9. The method according to claim 7, wherein such compound is 6-hydroxy-2-phenyl-5-(2,4,6-trimethylphenyl)-1,3-thiazin-4-one, 2-(4-fluorophenyl)-6-methoxycarbonyloxy-5-(2,4,6-trimethylphenyl)-1,3-thiazin-4-one, 2-(4-fluorophenyl)-6-hydroxy-5-(2,4,6-trimethylphenyl)-1,3-thiazin-4-one, 2-(4-trifluoromethylphenyl)-6-hydroxy-5-(2,4,6-trimethylphenyl)-1,3-thiazin-4-one, 2-(2-methylphenyl)-6-hydroxy-5-(2,4,6-trimethylphenyl)-1,3-thiazin-4-one, 2-(2-fluorophenyl)-6-hydroxy-5-(2,4,6-trimethylphenyl)-1,3-thiazin-4-one, 2-(4-fluorophenyl)-6-acetoxy-5-(2,4,6-trimethylphenyl)-1,3-thiazin-4-one, and 2-(4-fluorophenyl)-6-t-butylcarbonyloxy-5-(2,4,6-trimethylphenyl)-1,3-thiazin-4-one.

10. A compound according to claim 1, wherein such compound is 6-hydroxy-2-phenyl-5-(2,4,6-trimethylphenyl)-1,3-thiazin-4-one of the formula

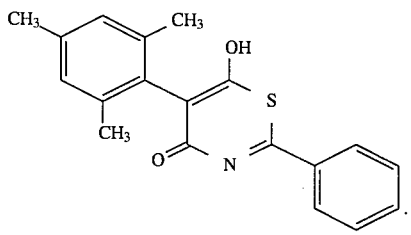

11. A compound according to claim 1, wherein such compound is 2-(4-fluorophenyl)-6-methoxycarbonyloxy-5-(2,4,6-trimethylphenyl)-1,3-thiazin-4-one of the formula

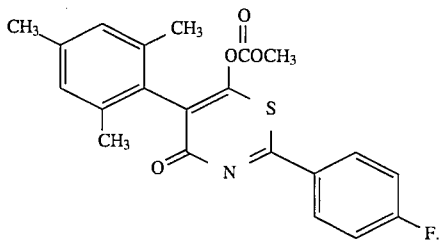

12. A compound according to claim 1, wherein such compound is 2-(4-fluorophenyl)-6-hydroxy-5-(2,4,6-trimethylphenyl)-1,3-thiazin-4-one of the formula

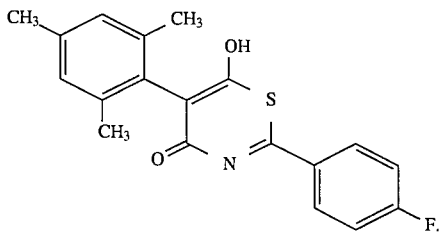

13. A compound according to claim 1, wherein such compound is 2-(4-trifluoromethylphenyl)-6-hydroxy-5-(2,4,6-trimethylphenyl)-1,3-thiazin-4-one of the formula

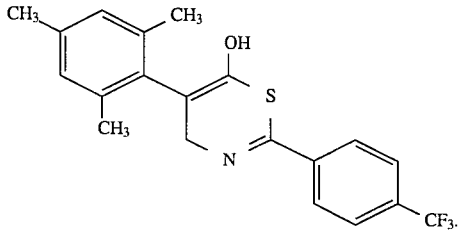

14. A compound according to claim 1, wherein such compound is 2-(2-methylphenyl)-6-hydroxy-5-(2,4,6-trimethylphenyl)-1,3-thiazin-4-one of the formula

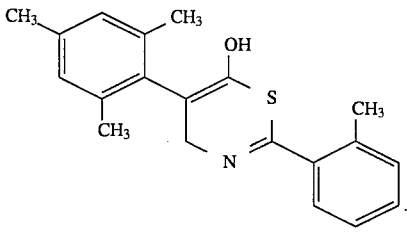

15. A compound according to claim 1, wherein such compound is 2-(2-fluorophenyl)-6-hydroxy-5-(2,4,6-trimethylphenyl)-1,3-thiazin-4-one of the formula

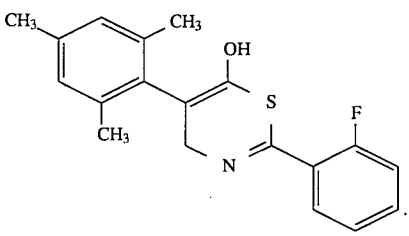

16. A compound according to claim 1, wherein such a compound is 2-(4-fluorophenyl)-6-acetoxy-5-(2,4,6-trimethylphenyl)-1,3-thiazin-4-one, wherein such compound is e of the formula

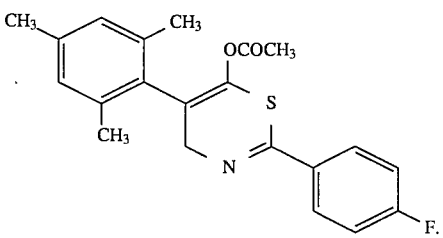

17. A compound according to claim 1, wherein such compound is 2-(4-fluorophenyl)-6-t-butylcarbonyloxy-5-(2,4,6-trimethylphenyl)-1,3-thiazin-4-one of the formula

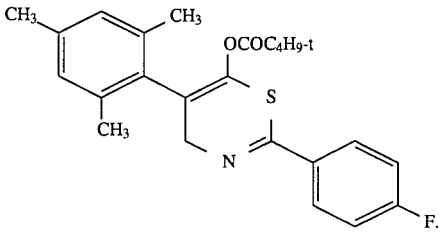

18. The method according to claim 6, wherein such compound is
6-hydroxy-2-phenyl-5-(2,4,6-trimethylphenyl)-1,3-thiazin-4-one, 2-(4-fluorophenyl)-6-methoxycarbonyloxy-5-(2,4,6-trimethylphenyl)-1,3-thiazin-4one,
2-(4-fluorophenyl)-6-hydroxy-5-(2,4,6-trimethylphenyl)-1,3-thiazin-4-one,
2-(4-trifluoromethylphenyl)-6-hydroxy-5-(2,4,6-trimethylphenyl)-1,3-thiazin-4-one,
2-(2-methylphenyl)-6-hydroxy-5-(2,4,6-trimethylphenyl)-1,3-thiazin-4-one,
2-(2-fluorophenyl)-6-hydroxy-5-(2,4,6-trimethylphenyl)-1,3-thiazin-4-one,
2-(4-fluorophenyl)-6-acetoxy-5-(2,4,6-trimethylphenyl)-1,3-thiazin-4-one, and
2-(4-fluorophenyl)-6-t-butylcarbonyloxy-5-(2,4,6-trimethylphenyl)-1,3-thiazin-4-one.

* * * * *

UNITED STATES PATENT AND TRADEMARK OFFICE
CERTIFICATE OF CORRECTION

PATENT NO. : 5,565,450
DATED : October 15, 1996
INVENTOR(S) : Fischer, et al.

It is certified that error appears in the above-indentified patent and that said Letters Patent is hereby corrected as shown below:

Col. 33, line 41  After " $C_1$-$C_6$-halogenoalkoxy; " delete " halogenoalkoxy; "

Col. 34, line 32  Delete " $C_3$-$C_1$-alkinythio " and substitute -- $C_3$-$C_6$-alkinylthio --

Col. 35, lines 57-  Delete " $C_1$-polyalkoxy-$C_1$-$C_6$-alkyl " and substitute -- $C_1$-$C_4$-polyalkoxy-$C_1$-$C_6$-alkyl --

Signed and Sealed this

Twenty-second Day of April, 1997

Attest:

BRUCE LEHMAN

*Commissioner of Patents and Trademarks*

*Attesting Officer*